(12) United States Patent
Sturis et al.

(10) Patent No.: US 12,343,383 B2
(45) Date of Patent: Jul. 1, 2025

(54) HIGH CONCENTRATION INSULIN FORMULATION

(71) Applicant: Novo Nordisk A/S, Bagsvaerd (DK)

(72) Inventors: Jeppe Sturis, Vaerloese (DK); Svend Havelund, Bagsvaerd (DK); Karen-Margrethe Pedersen, Copenhagen V (DK)

(73) Assignee: Novo Nordisk A/S, Bagsvaerd (DK)

( * ) Notice: Subject to any disclaimer, the term of this patent is extended or adjusted under 35 U.S.C. 154(b) by 633 days.

(21) Appl. No.: 17/626,025

(22) PCT Filed: Jul. 10, 2020

(86) PCT No.: PCT/EP2020/069512
§ 371 (c)(1),
(2) Date: Jan. 10, 2022

(87) PCT Pub. No.: WO2021/009027
PCT Pub. Date: Jan. 21, 2021

(65) Prior Publication Data
US 2022/0249619 A1 Aug. 11, 2022

(30) Foreign Application Priority Data
Jul. 12, 2019 (EP) .................... 19185958

(51) Int. Cl.
| | |
|---|---|
| *A61K 38/00* | (2006.01) |
| *A61K 9/00* | (2006.01) |
| *A61K 31/7084* | (2006.01) |
| *A61K 33/30* | (2006.01) |
| *A61K 38/28* | (2006.01) |
| *A61K 47/02* | (2006.01) |
| *A61K 47/18* | (2017.01) |
| *A61P 3/10* | (2006.01) |

(52) U.S. Cl.
CPC ............ *A61K 38/28* (2013.01); *A61K 9/0019* (2013.01); *A61K 31/7084* (2013.01); *A61K 33/30* (2013.01); *A61K 47/02* (2013.01); *A61K 47/18* (2013.01); *A61P 3/10* (2018.01)

(58) Field of Classification Search
CPC .................. A61K 38/28; A61K 9/0019; A61K 31/7084; A61K 33/30; A61K 47/02; A61K 47/18; A61P 3/10; C07K 14/62
See application file for complete search history.

(56) References Cited

U.S. PATENT DOCUMENTS

| | | |
|---|---|---|
| 3,528,960 A | 9/1970 | Haas |
| 3,868,358 A | 2/1975 | Jackson |
| 3,907,676 A | 9/1975 | Jorgensen |
| 4,476,118 A | 10/1984 | Brange et al. |
| 4,652,548 A | 3/1987 | Chance et al. |
| 4,669,430 A | 6/1987 | Reinold et al. |
| 4,764,592 A | 8/1988 | Massey et al. |
| 4,876,322 A | 10/1989 | Budde et al. |
| 4,983,658 A | 1/1991 | Kress et al. |
| 5,008,241 A | 4/1991 | Markussen et al. |
| 5,177,058 A | 1/1993 | Dorschug |
| 5,382,574 A | 1/1995 | Jorgensen |
| 5,605,884 A | 2/1997 | Lee et al. |
| 5,646,242 A | 7/1997 | Baker et al. |
| 5,750,497 A | 5/1998 | Havelund et al. |
| 5,830,999 A | 11/1998 | Dunn |
| 5,866,538 A | 2/1999 | Norup et al. |
| 5,898,067 A | 4/1999 | Balschmidt et al. |
| 5,905,140 A | 5/1999 | Hansen |
| 6,011,007 A | 1/2000 | Havelund et al. |
| 6,051,551 A | 4/2000 | Hughes et al. |
| 6,174,856 B1 | 1/2001 | Langballe et al. |
| 6,211,144 B1 | 4/2001 | Havelund |
| 6,221,837 B1 | 4/2001 | Ertl et al. |
| 6,251,856 B1 | 6/2001 | Markussen et al. |
| 6,335,316 B1 | 1/2002 | Hughes et al. |
| 6,451,762 B1 | 9/2002 | Havelund et al. |
| 6,451,970 B1 | 9/2002 | Schaffer et al. |
| 6,504,005 B1 | 1/2003 | Fridkin et al. |
| 6,620,780 B2 | 9/2003 | Markussen et al. |

(Continued)

FOREIGN PATENT DOCUMENTS

| | | |
|---|---|---|
| AU | 2011252127 B2 | 2/2014 |
| CN | 86101489 A | 1/1987 |

(Continued)

OTHER PUBLICATIONS

Lane W. S. et al., High-dose insulin therapy: is it time for U-500 insulin?, Endocrine Practice, Jan./Feb. 2009, vol. 15, No. 1, pp. 71-79.
Segal A. R. et al., Use of concentrated insulin human regular (U-500) for patients with diabetes, American Journal of Health-System Pharmacy, Sep. 15, 2010, vol. 67, No. 18, pp. 1526-1535.
Valentine V., Don't Resist Using U-500 Insulin and Pramlintide for Severe Insulin Resistance, Clinical Diabetes, Apr. 2012, vol. 30, No. 2, pp. 80-84.
Obesity Society: Your weight and diabetes—http://www.obesity.org/resources-for/your-weight-and-diabetes.htm, (accessed Jul. 21, 2015).
Inzucchi S. E. et al., Management of hyperglycemia in type 2 diabetes: a patient-centered approach. Position statement of the American Diabetes Association (ADA) and the European Association for the Study of Diabetes (EASD), Diabetologia, Apr. 20, 2012, vol. 55, No. 6, pp. 1577-1596.

(Continued)

*Primary Examiner* — Jeanette M Lieb
(74) *Attorney, Agent, or Firm* — Elizabeth A. Dingess-Hammond (57) ABSTRACT

The invention concerns a soluble insulin preparation comprising NεB29-hexadecandioyl-γ-Glu-(desB30) human insulin in a concentration from 1800 nmol/ml to 4200 nmol/ml, Zinc ions in a concentration from 4.0 Zn/6Ins to 7.0 Zn/6Ins, Niacinamide in a concentration from 110 mM to 220 mM or treprostinil in a concentration from 0.02 µg/ml to 1 µg/ml, Citrate in a concentration from 6 mM to 40 mM, and pH in the range from 7.0 to 8.0. The invention further comprises a method for using the soluble insulin preparation for reducing the blood glucose level in a mammal and a process for preparing the soluble insulin preparations.

20 Claims, 4 Drawing Sheets

(56) References Cited

U.S. PATENT DOCUMENTS

| | | |
|---|---|---|
| 6,652,886 B2 | 11/2003 | Ahn et al. |
| 6,869,930 B1 | 3/2005 | Havelund et al. |
| 7,229,964 B2 | 6/2007 | Markussen et al. |
| 7,402,565 B2 | 7/2008 | Kjeldsen et al. |
| 7,544,656 B2 | 6/2009 | Sabetsky |
| 7,615,532 B2 | 11/2009 | Jonassen et al. |
| 7,713,929 B2 | 5/2010 | Steiner et al. |
| 8,003,605 B2 | 8/2011 | Bayer et al. |
| 8,067,362 B2 | 11/2011 | Kodra et al. |
| 8,404,645 B2 | 3/2013 | Schlein |
| 8,691,759 B2 | 4/2014 | Madsen et al. |
| 8,722,620 B2 | 5/2014 | Fynbo et al. |
| 8,796,205 B2 | 8/2014 | Jonassen et al. |
| 8,828,923 B2 | 9/2014 | Jonassen et al. |
| 8,933,021 B2 | 1/2015 | Hubalek et al. |
| 8,962,794 B2 | 2/2015 | Madsen et al. |
| 9,034,818 B2 | 5/2015 | Poulsen et al. |
| 9,045,560 B2 | 6/2015 | Madsen et al. |
| 9,447,163 B2 | 9/2016 | Mollerup et al. |
| 9,481,721 B2 | 11/2016 | Naver et al. |
| 9,603,904 B2 | 3/2017 | Johansen et al. |
| 9,688,737 B2 | 6/2017 | Madsen et al. |
| 9,839,579 B2 | 12/2017 | Weeks et al. |
| 9,884,094 B2 | 2/2018 | Johansen et al. |
| 10,137,172 B2 | 11/2018 | Johansen et al. |
| 10,172,922 B2 | 1/2019 | Christe et al. |
| 10,925,931 B2 | 2/2021 | Akers et al. |
| 11,167,035 B2 | 11/2021 | Havelund et al. |
| 2001/0036916 A1 | 11/2001 | Brader |
| 2002/0045731 A1 | 4/2002 | Schaffer et al. |
| 2002/0155994 A1 | 10/2002 | Havelund et al. |
| 2003/0004096 A1 | 1/2003 | Boderke |
| 2003/0236196 A1 | 12/2003 | Kerwin et al. |
| 2004/0006000 A1 | 1/2004 | Langkjaer |
| 2004/0037909 A1 | 2/2004 | Kim et al. |
| 2004/0116345 A1 | 6/2004 | Besman et al. |
| 2004/0138099 A1 | 7/2004 | Draeger |
| 2005/0054818 A1 | 3/2005 | Brader et al. |
| 2005/0074866 A1 | 4/2005 | Grancha et al. |
| 2005/0222006 A1 | 10/2005 | Havelund et al. |
| 2005/0232899 A1 | 10/2005 | Balwani et al. |
| 2006/0183668 A1 | 8/2006 | Jonassen et al. |
| 2008/0076705 A1 | 3/2008 | Kodra et al. |
| 2009/0074882 A1 | 3/2009 | Havelund et al. |
| 2009/0137454 A1 | 5/2009 | Fynbo et al. |
| 2009/0186807 A1 | 7/2009 | Boderke |
| 2009/0239785 A1 | 9/2009 | Hubalek et al. |
| 2009/0312236 A1 | 12/2009 | Beals et al. |
| 2010/0009899 A1 | 1/2010 | Jonassen et al. |
| 2010/0167990 A1 | 7/2010 | Poulsen et al. |
| 2011/0152185 A1 | 6/2011 | Plum et al. |
| 2011/0230402 A1 | 9/2011 | Johansen et al. |
| 2011/0301081 A1 | 12/2011 | Becker et al. |
| 2012/0245085 A1 | 9/2012 | Naver et al. |
| 2013/0261051 A1 | 10/2013 | Johansen |
| 2014/0073759 A1 | 3/2014 | Mollerup et al. |
| 2014/0328943 A1 | 11/2014 | Havelund et al. |
| 2014/0349925 A1 | 11/2014 | Jonassen et al. |
| 2015/0126439 A1 | 5/2015 | Johansen et al. |
| 2015/0250857 A1 | 9/2015 | Andresen et al. |
| 2015/0273022 A1 | 10/2015 | Wilson et al. |
| 2016/0058840 A1 | 3/2016 | Johansen et al. |
| 2016/0296602 A1 | 10/2016 | Johansen |
| 2017/0056478 A1 | 3/2017 | Akers et al. |
| 2017/0165327 A1 | 6/2017 | Andresen et al. |
| 2017/0319664 A1 | 11/2017 | Johansen |
| 2018/0125946 A1 | 5/2018 | Johansen |
| 2019/0112348 A1 | 4/2019 | Madsen et al. |
| 2019/0160155 A1 | 5/2019 | Johansen |
| 2019/0194285 A1 | 6/2019 | Olsen et al. |
| 2019/0374614 A1 | 12/2019 | Skibsted et al. |
| 2021/0060132 A1 | 3/2021 | Andresen et al. |
| 2022/0152160 A1 | 5/2022 | Johansen |

FOREIGN PATENT DOCUMENTS

| | | |
|---|---|---|
| CN | 88102311 A | 11/1988 |
| CN | 1829738 A | 9/2006 |
| CN | 101389650 A | 12/2006 |
| CN | 101454019 A | 6/2009 |
| CN | 104892749 A | 9/2015 |
| CN | 107920992 A | 4/2018 |
| DE | 1212679 B | 3/1966 |
| EP | 214826 A2 | 3/1987 |
| EP | 315968 A1 | 5/1989 |
| EP | 375437 A2 | 6/1990 |
| EP | 383472 A2 | 8/1990 |
| EP | 420649 A2 | 4/1991 |
| EP | 818204 A2 | 1/1998 |
| EP | 925792 A2 | 6/1999 |
| EP | 1153608 A1 | 11/2001 |
| EP | 884053 B1 | 10/2002 |
| EP | 1283051 A1 | 2/2003 |
| EP | 0894095 | 5/2003 |
| EP | 0785713 B1 | 9/2003 |
| EP | 1595544 A1 | 11/2005 |
| EP | 2107069 A2 | 10/2009 |
| EP | 1951198 B1 | 6/2010 |
| EP | 2264065 A2 | 12/2010 |
| EP | 2264066 A2 | 12/2010 |
| EP | 2275439 A2 | 1/2011 |
| EP | 2287184 A2 | 2/2011 |
| EP | 2387989 A2 | 11/2011 |
| EP | 2389945 A1 | 11/2011 |
| EP | 2505593 A1 | 10/2012 |
| GB | 1042194 A | 9/1966 |
| GB | 1492997 | 11/1977 |
| JP | B S36-11994 | 7/1961 |
| JP | 38005689 | 5/1963 |
| JP | B S38-5689 | 5/1963 |
| JP | S5767548 A | 4/1982 |
| JP | H01254699 A | 10/1989 |
| JP | 02101022 | 4/1990 |
| JP | H09502867 | 3/1997 |
| JP | H10509176 | 8/1998 |
| JP | 11-502110 | 2/1999 |
| JP | 2000-501419 A | 2/2000 |
| JP | 2000-504732 A | 4/2000 |
| JP | 2000-515542 | 11/2000 |
| JP | 2001-518915 A | 10/2001 |
| JP | 2001-518916 A | 10/2001 |
| JP | 2001-521004 A | 11/2001 |
| JP | 2001-521904 A | 11/2001 |
| JP | 2001521006 A | 11/2001 |
| JP | 2001-526225 A | 12/2001 |
| JP | 2002-527487 A | 8/2002 |
| JP | 2002-308899 A | 10/2002 |
| JP | 2002-543092 A | 12/2002 |
| JP | 2004-523589 A | 8/2004 |
| JP | 2006-511441 A | 4/2006 |
| JP | 2006-519253 | 8/2006 |
| JP | 2007-523881 | 8/2007 |
| JP | 2009-522231 | 6/2009 |
| JP | 4808785 B2 | 11/2011 |
| JP | 4959005 B2 | 6/2012 |
| JP | 5026567 B2 | 9/2012 |
| JP | 5331071 B2 | 10/2013 |
| JP | 2016523807 A | 8/2016 |
| RU | 2160118 C2 | 12/2000 |
| RU | 2164520 C2 | 3/2001 |
| RU | 2006103280 A | 9/2007 |
| RU | 2317821 C2 | 2/2008 |
| RU | 2352581 C2 | 4/2009 |
| WO | 91/09617 A1 | 7/1991 |
| WO | 91/12817 A1 | 9/1991 |
| WO | 9307922 A1 | 4/1993 |
| WO | 93/12812 A1 | 7/1993 |
| WO | 95/07931 A1 | 3/1995 |
| WO | 95/32730 A1 | 12/1995 |
| WO | 96/10417 A1 | 4/1996 |
| WO | 96/29344 | 9/1996 |
| WO | 97/04801 A1 | 2/1997 |
| WO | 97/31022 A1 | 8/1997 |

(56) References Cited

FOREIGN PATENT DOCUMENTS

| | | |
|---|---|---|
| WO | 98/02460 A1 | 1/1998 |
| WO | 98/05361 A2 | 2/1998 |
| WO | 98/42367 A1 | 10/1998 |
| WO | 98/42368 A1 | 10/1998 |
| WO | 98/47529 A1 | 10/1998 |
| WO | 99/21573 | 5/1999 |
| WO | 99/21578 | 5/1999 |
| WO | 99/21888 A1 | 5/1999 |
| WO | 99/22754 | 5/1999 |
| WO | 99/24071 A1 | 5/1999 |
| WO | 99/32116 A1 | 7/1999 |
| WO | 00/23098 A1 | 4/2000 |
| WO | 00/43034 A2 | 7/2000 |
| WO | 00/64940 | 11/2000 |
| WO | 2001/49314 A2 | 7/2001 |
| WO | 02076495 A1 | 10/2002 |
| WO | 2003/002136 A2 | 1/2003 |
| WO | 03/013573 | 2/2003 |
| WO | 03030829 A2 | 4/2003 |
| WO | 03/053339 A2 | 7/2003 |
| WO | 03/0053339 A2 | 7/2003 |
| WO | 03/094951 A1 | 11/2003 |
| WO | 03/094956 A1 | 11/2003 |
| WO | 2004/039392 A2 | 5/2004 |
| WO | 2004074481 | 9/2004 |
| WO | 2004/112828 A1 | 12/2004 |
| WO | 2005/005477 A2 | 1/2005 |
| WO | 2005/012347 A2 | 2/2005 |
| WO | 2005/016365 A2 | 2/2005 |
| WO | 2005/021022 A2 | 3/2005 |
| WO | 2005/47508 A1 | 5/2005 |
| WO | 2005/063298 A1 | 7/2005 |
| WO | 2005/089722 A1 | 9/2005 |
| WO | 2005/117948 A1 | 12/2005 |
| WO | 2006/008238 A1 | 1/2006 |
| WO | 2006/020720 A2 | 2/2006 |
| WO | 2006/023665 A2 | 3/2006 |
| WO | 06/51103 A2 | 5/2006 |
| WO | 2006/053906 A1 | 5/2006 |
| WO | 2006/079019 A2 | 7/2006 |
| WO | 2006/082204 | 8/2006 |
| WO | 2006/082205 | 8/2006 |
| WO | 2007/041481 A1 | 4/2007 |
| WO | 07/074133 A2 | 7/2007 |
| WO | 2007/074133 A2 | 7/2007 |
| WO | 2007096431 A1 | 8/2007 |
| WO | 2007/121256 A2 | 10/2007 |
| WO | 2007/128815 A1 | 11/2007 |
| WO | 2007/128817 A2 | 11/2007 |
| WO | 07135117 A2 | 11/2007 |
| WO | 2008/034881 A1 | 3/2008 |
| WO | 2008/132224 A2 | 11/2008 |
| WO | 2008/152106 A1 | 12/2008 |
| WO | 2009/060071 A1 | 5/2009 |
| WO | 2009/063072 A2 | 5/2009 |
| WO | 2010049488 A1 | 5/2010 |
| WO | 2011051486 A2 | 5/2011 |
| WO | 2011141407 A1 | 11/2011 |
| WO | 2012055967 A2 | 5/2012 |
| WO | 2012080320 A1 | 6/2012 |
| WO | 2012119007 A1 | 9/2012 |
| WO | 2013037754 A2 | 3/2013 |
| WO | 2013164375 A1 | 11/2013 |
| WO | 2018007172 A1 | 1/2018 |
| WO | 2018060735 A1 | 4/2018 |
| WO | 2019072818 A1 | 4/2019 |

OTHER PUBLICATIONS

Crasto W et al., Insulin U-500 in severe insulin resistance in type 2 diabetes mellitus, Postgraduate Medical Journal, Feb. 10, 2009, vol. 85, No. 1002, pp. 219-222.
Heise T et al., Insulin Degludec Has a Two-Fold Longer Half-Life and a More Consistent Pharmacokinetic Profile Than Insulin Glargine, Diabetes, 2011, vol. 60(Suppl 1), LB11, (Abstract 37-LB), accessed Oct. 9, 2019.
Nosek L. et al., Ultra-Long-Acting Insulin Degludec Has a Flat and Stable Glucose-Lowering Effect, Diabetes 2011, 60(Suppl 1), LB14 (Abstract 49-LB), accessed Oct. 9, 2019.
Korsatko S. et al., Ultra-Long-Acting Insulin Degludec: Two Different Formulations (U100 and U200) Are Bioequivalent and Show Similar Pharmacodynamics, Diabetes 2011, 60(Suppl 1), A624 (Abstract 2349-PO), accessed Oct. 9, 2019.
Zinman B. et al., Insulin degludec, an ultra-long-acting basal insulin, once a day or three times a week versus insulin glargine once a day in patients with type 2 diabetes: a 16-week, randomized, open-label, phase 2 trial. The Lancet, Mar. 10, 2011, vol. 377, 924-931.
Heller S. et al., Insulin degludec, an ultra-longacting basal insulin, versus insulin glargine in basal-bolus treatment with mealtime insulin aspart in type 1 diabetes (BEGIN Basal-Bolus Type 1): a phase 3, randomised, open-label, treat-to-target non-inferiority trial, The Lancet, Apr. 2012, vol. 379, pp. 1489-1497.
Garber A. J. et al., Insulin degludec, an ultra-longacting basal insulin, versus insulin glargine in basal-bolus treatment with mealtime insulin aspart in type 2 diabetes (BEGIN Basal-Bolus Type 2): a phase 3, randomised, open-label, treat-to-target non-inferiority trial, The Lancet, Apr. 2012, vol. 379, pp. 1498-1507.
Declaration of Helsinki, Ethical principles for medical research involving human subjects., Journal of Indian Medical Association, Jun. 2009, vol. 107, No. 6, pp. 403-405.
Defining and Reporting Hypoglycemia in Diabetes: A report from the American Diabetes Association Workgroup on Hypoglycemia, Diabetes Care, 2005, vol. 28, No. 5, pp. 1245-1249.
HUMULIN® R Regular U-500 (Concentrated), Insulin Human Injection, USP (rDNA Origin), Eli Lilly and Company, Lilly USA, LLC, Indianapolis, IN 46285, USA, 1996.
Thornton S. et al., Intravenous overdose of insulin glargine without prolonged hypoglycemic effects, The Journal of Emergency Medicine, Sep. 2012, vol. 43, No. 3, pp. 435-437, XP002711646.
Zinman B. et al., Insulin degludec versus insulin glargine in insulin-naive patients with type 2 diabetes: a 1-year, randomized, treat-to-target trial (BEGIN Once long), Diabetes Care, Dec. 2012, vol. 35, No. 12, pp. 2464-2471, XP9172018.
Rodbard H et al., Reduced risk of hypoglycaemia with insulin degludec vs insulin glargine in patients with type 2 diabetes requiring high doses of basal insulin: meta-analysis of five randomized trials. Presented as an oral at the AACE 21st Annual Scientific and Clinical Congress, Philadelphia, PA, May 23, 2012, (Abstract 241).
ICH Harmonised Tripartite Guideline: Guideline for Good Clinical Practice, Journal of postgraduate medicine, 2001, vol. 47, No. 3, pp. 199-203.
Marcus A., Diabetes care—insulin delivery in a changing world, The Medscape Journal of Medicine, 2008, vol. 10, No. 5, 120.
Hoevelmann U. et al., Insulin degludec 200 U/ml is ultra-lang-acting and has a flat and stable glucose-lowering effect, Diabetologia, 2012, vol. 55, No. Suppl. 1, pp. S374-S375, XP002723769 & 48th Annual Meeting of the European-Association-For-The-Study-Of-Diabetes; Berlin, Germany; Oct. 1-5, 2012.
Wang F. et al., Insulin degludec as an ultralong-acting basal insulin once a day: a systematic review, Diabetes, Metabolic Syndrome and Obesity : Targets and Therapy, Jul. 2012, vol. 5, pp. 191-204, XP002723770.
Korsatko S. et al., Ultra-long-acting insulin degludec: bioequivalence and similar pharmacodynamics shown for two different formulations (U100 and U200), Diabetologia, 2011, vol. 54, No. Suppl. 1, XP002723771, p. S427, & 47th Annual Meeting of the European-Association-For-The-Study-Of-Diabetes (EASD); Lisbon, Portugal; Sep. 12-16, 2011.
Havelund, S. et al., "The Mechanism of Protraction of Insulin Detemir, a Long-Acting, Acylated Analog of Human Insulin", Pharmaceutical Research, 2004, vol. 21, No. 8, pp. 1498-1504.
Barnett, A.H., "A Review of Basal Insulins," Diabet Med, 2003, vol. 20, No. 11, pp. 873-885.

(56) References Cited

OTHER PUBLICATIONS

Brussels: International Diabetes Federation, IDF Clinical Guidelines Task Force, Guideline for Management of Postmeal Glucose, 2007, pp. 1-32, http://www.idf.org/webdata/docs/Guideline_PMG_final.pdf.

Brussels: International Diabetes Federation, IDF Clinical Guidelines Task Force, Global Guideline for Type 2 Diabetes, 2005, pp. 1-82, http://www.idf.org/webdata/docs/IDF%20GGT2D.pdf.

Irie et al., "Pharmacokinetics and Pharmacodynamics of Single Dose Insulin Detemir, Long-Acting Soluble Insulin Analogue Compared to NPH Insulin in Patients With Type 1 Diabetes Mellitus", J Clin Ther Med, 2007, vol. 23, No. 5, pp. 349-356.

Schlichtkrull, J., "Insulin Crystals", Acta Chemica Scandinavica, 1956, vol. 10, No. 9, pp. 1455-1458.

Vajo et al., "Genetically Engineered Insulin Analogs: Diabetes in the New Millennium," Pharma Rev, 2000, vol. 52, No. 1, pp. 1-9.

Whittingham, J.L. et al., "Crystallographic and Solution Studies of N-Lithocholyl Insulin: A New Generation of prolonged-Acting Human Insulins", Biochemistry, 2004, vol. 42, pp. 5987-5995.

Brange, J et al Diabetic Medicine Neutral Insulin Solutions Physically Stabilized by Addition of ZN2+, 1986, vol. 3, No. 6, pp. 532-536.

Jonassen, I. et al., Pharmaceutical Research 2006, vol. 23, No. 1, pp. 49-55.

Yasuhiko Iwamoto, "New Insulin Formulation," Annual Review Increation and Metabolism 2000, 9 pages.

Nathan, D. M. et al., "Management of Hyperglycemia in Type 2 Diabetes: A Consensus Algorithm for the Initiation and Adjustment of Therapy," Diabetes Care, 2008, vol. 31, No. 1, pp. 173-175.

Heise, T. et al., "Towards Peakless, Reproducible and Long-Acting Insulins. An Assessment of the Basal Analogues Based on Isoglycaemic Clamp Studies," Diabetes Obes Metab, 2007, vol. 9, No. 5, pp. 648-659.

Hinds et al., "PEGylated insulin in PLGA microparticles. In vivo and in vitro analysis," Journal of Controlled Release, 2005, vol. 104, No. 3, pp. 447-460.

Heller. S R, Current Medical Research and Opinion, "Insulin Analogues", 2002, vol. 18, No. 1, pp. 40-47.

R. Cuddihy et al., Diabetologia, "Once-Daily Use of a New Generation Ultra-Long Acting Basal Insulin With a Bolus Boost in Insulin-Naïve People With Type 2 Diabetes: Comparison With Insulin Glargine", Sep. 2010, vol. 53, No. 1, pp. S389.

Samuel et al. "Studies on the immunogenicity of protamines in humans and experimental animals by means of a micro-complement fixation test." Clin. Exp. Immunol. vol. 33: pp. 252-260. 1978.

Kurtz et al. "Circulating IgG antibody to protamine in patients treated with protamine-insulins." Diabetologica. vol. 25: pp. 322-324. 1983.

Definition of Moiety From http://dictionary.reference.com/browse/moiety, Aug. 26, 2010, pp. 1-3.

I. Jonassen et al., "Insulin Degludec: Multi-Hexamer Formation is the Underlying Basis for This New Generation Ultra-Long Acting Basal Insulin", Diabetologia, Sep. 2010, vol. 53, No. 1, pp. S388.

R. Cuddihy et al., "Once-Daily Use of a New Generation Ultra-Long Acting Basal Insulin With a Bolus Boost in Insulin-Naïve People With Type 2 Diabetes: Comparison With Insulin Glargine". Diabetologia, Sep. 2010, vol. 53, No. 1, pp. S389.

American Diabetes Association, Standards of Medical Care in Diabetes Jan. 2012, Diabetes Care 2012, vol. 35 (Suppl 1), pp. S11-S63.

American Diabetes Association. Insulin administration. Diabetes Care, Jan. 2012 , vol. 35, No. 1, pp. S1-S2.

American Diabetes Association. Standards of Medical Care in Diabetes—2014. Diabetes Care. 2014, vol. 37 Suppl 1, pp. S14-S80.

Anderson RM et al. Patient empowerment: results of a randomized controlled trial. Diabetes Care. 1995, vol. 18, No. 7 pp. 943-949.

Barnett et al: Dosing of insulin glargine in the treatment of type 2 diabetes ,Clinical Therapeutics, 2007 vol. 29, No. 6,,pp. 987-999.

Benjamin EM. Self-monitoring of blood glucose: the basics. Clinical Diabetes. 2002, vol. 20, No. 1, pp. 45-47.

Schnell et al., "Consensus statement on self-monitoring of blood glucose in diabetes," Diabetes, Stoffwechsel und Herz, Jul. 2009, vol. 4, pp. 285-289.

Selvin et al., ""Meta-Analysis: Glycosylated Hemoglobin and Cardiovascular Disease in Diabetes Mellitus,"" Ann. Intern. Med., Sep. 2004, vol. 141, pp. 421-431.

The Diabetes Control and Complications Trial Research Group, "The effect of intensive treatment of diabetes on the development and progression of long-term complications in insulin-dependent diabetes mellitus," N Engl J Med, 1993, vol. 329, No. 14, pp. 977-986.

UK Prospective Diabetes Study (UKPDS) Group, "Intensive blood-glucose control with sulphonylureas or insulin compared with conventional treatment and risk of complications in patients with type 2 diabetes (UKPDS 33)," Lancet, 1998, vol. 352, pp. 837-853.

Yeaw et al., "Cost of self monitoring of blood glucose in Canada among patients on an insulin regimen for diabetes," Diabetes Ther. Epub Jun. 27, 2012, vol. 3, pp. 1-17.

Yeaw et al., "Cost of self-monitoring of blood glucose in the United States among patients on an insulin regimen for diabetes," J Manag. Care Pharm., Jan. Feb. 2012, vol. 18, pp. 21?32.

Yeaw et al., "Self-monitoring blood glucose test strip utilization in Canada," Diabetes, Jun. 2012, vol. 61(Suppl 1), p. A35.

Lajara R, et al. Healthcare professional and patient perceptions of a new prefilled insulin pen versus vial and syringe. Expert Opinion on Drug Delivery, Sep. 2012, vol. 9, pp. 1181-1196.

Bailey T, et al. FlexTouch® for the delivery of insulin: technical attributes and perception among patients and healthcare professionals. Expert Review of Medical Devices, 2012, vol. 9, pp. 209-217, published online Jan. 9, 2014.

Anthony H. Barnett, Diabetic Medicine, A Review of Basal Insulins, 2003, vol. 20, No. 11, pp. 873-885.

Heise, T. et al., Diabetes, Obesity and Metabolism, Towards Peakless, Reproducible and Long-Acting Insulins. An Assessment of the Basal Analogues Based on Isoglycaemic Clamp Studies, 2007, vol. 9, No. 5, pp. 648-659.

IDF Clinical Guidelines Task Force, Brussels: International Diabetes Federation 2005, Global Guideline for Type 2 Diabetes, 2005.

IDF Clinical Guidelines Task Force, Brussels: International Diabetes Federation 2007, Guideline for Management of Postmeal Glucose, 2007.

Nathan, D. M. et al., Diabetes Care, Management of Hyperglycemia in Type 2 Diabetes: A Consensus Algorithm for the Initiation and Adjustment of Therapy, 2008, vol. 31, No. 1, pp. 173-175.

Talboys Catalog, 2008 Laboratory Equipment Catalog, Talboys by Troemner, 122 pages (2008).

Heise et al "Lower Within-Subject Variability of Insulin Detemir in Comparison to NPH Insulin an Insulin Glargine in People with Type 1 Diabetes" Diabetes, 2004, vol. 53, pp. 1614-1620.

Novo Nordisk, Levemir Product Information, Jun. 16, 2005. 42 pages.

"America Pink", http://america.pink/insulin-degludec_2091149.html, downloaded Aug. 24, 2016.

L. Heinemann and J. H. Anderson Jr. Diabetes Technol Ther 6 (5):698-728, 2004.

Living with Diabetes, available at http://www.diabetes.org/living-with-diabetes/treatment-and-care/medication/?loc=lwd-slabnav, accessed on Jan. 5, 2017.

WebMD "What is a unit of insulin," available at http://answers.webmd.com/answers/1196453/what-is-a-unit-of-insulin, accessed Nov. 8, 2018.

Heise et al., "Insulin Degludec 200 U/mL is Ultra-Long Acting and Has a Flat and Stable Glucose-Lowering Effect," Canadian Journal of Diabetes, Oct. 2012, vol. 36, No. 5, p. S13.

Springer et al., "Management of Type 2 Diabetes Mellitus in Children and Adolescents", Pediatrics, Feb. 2013, vol. 131, No. 2, pp. e648-e664.

Heise et al., "Ultra-Long-Acting Insulin Degludec has a Flat and Stable Glucose-Lowering Effect in Type 2 Diabetes," Diabetes, Obesity and Metabolism, Jun. 2012, vol. 14, pp. 944-950.

(56) References Cited

OTHER PUBLICATIONS

Heller et al., "Insulin Degludec, an Ultra-Longacting Basal Insulin, Versus Insulin Glargine . . . : a Phase 3, Randomized, Open-Label, Treat-to-Target Non-Inferiority Trial," The Lancet, Apr. 2012, vol. 379, pp. 1489-1497.

Tambascia et al., "Degludec: the new ultra-long insulin analogue," Diabetology Metabol. Synd., Jun. 2015, vol. 7, pp. 1-7.

Brange "Stability of Insulin", 1994, Kluwer Academic Publishers BV, pp. 30-31.

Birkeland et al."Insulin degludec in type 1 diabetes: a randomized controlled trial of a new-generation ultra-long-acting insulin compared with insulin glargine." Diabetes Care, Mar. 2011, vol. 34, No. 3, p. 661-665.

Briscoe et al.,"Hypoglycemia in type 1 and type 2 diabetes: physiology, pathophysiology, and management." Clinical diabetes, Jul. 2006, vol. 24, No. 3, pp. 115-121.

U.S. Appl. No. 16/463,594, filed May 23, 2019.

Le Tourneau, et al., "Dose escalation methods in phase 1 cancer clinical trials." JNCI: Journal of the National Cancer Institute, May 2009, vol. 101, No. 10, pp. 708-720.

American Diabetes Association, "Standards of Medical Care in Diabetes—2012," Diabet. Care., 2012, vol. 35(Suppl 1), pp. S11-S63.

American Diabetes Association, "Introduction," Diabetes Care, Jan. 2012, vol. 35(Suppl. 1), pp. S1-S2.

American Diabetes Association, "Standards of Medical Care in Diabetes—2014," Diabetes Care, Jan. 2014, vol. 37, Suppl. 1.

American Diabetes Association, "Insulin Administration," Diabetes Care, Jan. 2002, vol. 25(suppl 1), pp. S112-S115.

Anderson et al., "Patient empowerment: results of a randomized controlled trial," Diabetes Care, Jul. 1995, vol. 18, No. 7, pp. 943-949.

Benjamin EM, "Self-monitoring of blood glucose: the basics," Clin Diabetes, Jan. 2002, vol. 20, No. 1, pp. 45-47.

Canadian Diabetes Association Clinical Practice Guidelines Expert Committee, Canadian Diabetes Association, Can J Diabetes, Sep. 2008; vol. 32(Suppl 1), pp. S1-S201.

Davies et al., "Improvement of glycemic control in subjects with poorly controlled type 2 diabetes," Diabet. Care., Jun. 2005, vol. 28, pp. 1282-1288.

Duckworth et al., "Glucose control and vascular complications in veterans with type 2 diabetes," N Engl J Med, 2009, vol. 360, pp. 129-139.

Gerstein et al., "A randomized trial of adding insulin glargine vs. avoidance of insulin in people with Type 2 diabetes on either no oral glucose-lowering agents or submaximal doses of metformin and/or sulphonylureas. The Canadian INSIGHT (Implementing New Strategies with Insulin Glargine for Hyperglycaemia Treatment) Study," Diabet. Med., May 2006, vol. 23, No. 7, pp. 736-742.

Holman et al., "10-year follow-up of intensive glucose control in type 2 diabetes," N Engl J Med, 2008, vol. 359, pp. 1577-1589.

Holman et al., "A practical guide to basal and prandial insulin therapy," Diabet. Med., Jan. 1985, vol. 2, No. 1, pp. 45-53.

International Diabetes Federation Clinical Guidelines Task Force, "Global Guideline for Type 2 Diabetes," 2005.

Inzucchi et al., "Management of hyperglycemia in type 2 diabetes: a patient-centered approach: position statement of the American Diabetes Association (ADA) and the European Association for the Study of Diabetes (EASD)," Diabetes Care. Jun. 2012, vol. 35, pp. 1364-1379.

Kulzer et al., "Effects of self-management training in type 2 diabetes: a randomized, prospective trial," Diabet. Med., Feb. 2007, vol. 24, pp. 415-423.

LANTUS® (insulin glargine [rDNA origin] injection), Sanofi-aventis U.S. LLC, Bridgewater, NJ, USA; 2007, Health Care Professional, Dosing & Titration, accessed Jan. 17, 2019.

Liebl et al., "Direct costs and health-related resource utilisation in the 6 months after insulin initiation in German patients with type 2 diabetes mellitus in 2006: INSTIGATE study," Curr Med Res Opin, Jul. 2008, vol. 24, No. 8, pp. 2349-2358.

Meneghini et al., "The usage of a simplified self-titration dosing guideline (303 Algorithm) for insulin detemir in patients with type 2 diabetes—results of the randomized, controlled PREDICTIVETM 303 study," Diabet. Obes. Metab., Oct. 2007, vol. 9, pp. 902-913.

Nathan et al., ""Intensive Diabetes Treatment and Cardiovascular Disease in Patients with Type 1 Diabetes,"" N Engl. J Med., Dec. 2005, vol. 353, No. 25, pp. 2643-2653.

Nathan et al., "Management of hyperglycemia in type 2 diabetes: a consensus algorithm for the initiation and adjustment of therapy: update regarding thiazolidinediones: a consensus statement from the American Diabetes Association and the European Association for the Study of Diabetes," Diabetes Care, 2008, vol. 31, No. 1, pp. 173-175.

Norris et al., "Self-management education for adults with type 2 diabetes: a meta-analysis on the effect of glycemic control," Diabetes Care, Jul. 2002, vol. 25, pp. 1159-1171.

Ohkubo et al., "Intensive insulin therapy prevents the progression of diabetic microvascular complications in Japanese patients with non-insulin-dependent diabetes mellitus: a randomized prospective 6-year study," Diabetes Res. Clin. Pract., 1995, vol. 28, pp. 103-117.

Patel et al. "Intensive blood glucose control and vascular outcomes in patients with type 2 diabetes," N Engl. J Med, 2008, vol. 358, pp. 2560-2572.

Peyrot et al., "Factors associated with injection omission/non-adherence in the Global Attitudes of Patients and Physicians in Insulin Therapy Study," Diabet. Obes. Metab., Jun. 2012, vol. 14, pp. 1081?1087.

Peyrot et al., "Insulin adherence behaviors and barriers in the multinational Global Attitudes of Patients and Physicians in insulin therapy study," Diabet. Med., Feb. 2012, vol. 29, pp. 682?690.

Philis-Tsimikas et al, Insulin Degludec Once-Daily in Type 2 Diabetes: Simple or Step-Wise Titration (BEGIN: Once Simple Use), Advances in Therapy, Jun. 2013, vol. 30, No. 6, pp. 607-622.

Canadian Diabetes Association Clinical Practice Guidelines Expert Committee. Canadian Diabetes Association. Canadian Journal of Diabetes. 2008, vol. 32(Suppl 1)pp. S1-S201.

Davies M, et al.. Improvement of glycemic control in subjects with poorly controlled type 2 diabetes. Diabetes Care. 2005,vol. 28, No. 6, pp. 1282-1288.

Deutsch T et al.Utopia: A Consultation System for Visit-By-Visit Diabetes Management, Medical Informatica. Taylor and Francis.; Basingstoke. GB, 1996, vol. 21, No. 4, pp. 345-358.

Duckworth W. et al.Glucose Control and Vascular Complications in Veterans with Type 2 Diabetes, The new england journal o f medicine, Jan. 2009, vol. 360, pp. 129-139.

Gerstein H C et al. A randomized trial of adding insulin glargine vs.avoidance of insulin in people with Type 2 diabetes on either no oral glucose-lowering agents or submaximal doses of metformin and/or sulphonylureas. The Canadian INSIGHT (Implementing New Strategies with Insulin Glargine for Hyperglycaemia treatment) Study, Diabetic Medicines, 2006, vol. 23, No. 7, pp. 736-742.

Holman RR et al.,10-Year Follow-up of Intensive Glucose Control in Type 2 Diabetes,The New England Journal of Medicine, 2008, vol. 359, pp. 1577-1589.

Holman RR et al.A practical guide to Basal and Prandial Insulin therapy, Diabetic Medicine, 1985, vol. 2, pp. 45-53.

International Diabetes Federation Clinical Guidelines Task Force. Global Guideline for Type 2 Diabetes. 2005. Available at: http://www.idf.org/webdata/docs/IDF%20GGT2D.pdf. Accessed Dec. 19, 2012.

Inzucchi SE et al.Management of Hyperglycemia in Type 2 Diabetes: A Patient-Centered Approach: Position Statement of the American Diabetes Association (ADA) and the European Association for the Study of Diabetes (EASD),Diabetes care, Jun. 2012, vol. 35, pp. 1364-1379.

Iwamoto Yasuhi KO et al: Insulin degludec in Japanese patients with type 1 diabetes mellitus: A randomized controlled trial,Journal of Diabetes Investigation, Jan. 2013, vol. 4, No. 1, pp. 62-68.

Janka Hans U et al, Combination of oral antidiabetic agents with basal insulin; versus premixed insulin alone in randomized elderly patients with type 2 diabetes mellitus, Journal of the American Geriatrics Society, 2007,vol. 55, No. 2, pp. 182-188.

(56) References Cited

OTHER PUBLICATIONS

Kulzer B, et al. Effects of self-management training in type 2 diabetes: a randomized, prospective trial. Diabetic Medicine. 2007, vol. 24, No. 4, pp. 415-423.

LANTUS® (insulin glargine [rDNA origin] injection). sanofi-aventis U.S. LLC, Bridgewater, NJ, USA; 2007. Health Care Professional. Dosing & Titration. Available at: http://www.lantus.com/hcp/titration.aspx. Accessed Nov. 13, 2012.

Liebl A, et al. Direct costs and health-related resource utilisation in the 6 months after insulin initiation in German patients with type 2 diabetes mellitus in 2006: INSTIGATE study. Current Medical Research Opinion 2008, vol. 24, No. 3, pp. 2349-2358.

Meneghini L et al., The usage of a simplified self-titration dosing guideline (303 Algorithm) for insulin detemir in patients with type 2 diabetes-results of the randomized, controlled PREDICTIVE TM 303 study. Diabetes Obesity and Metabolism. 2007, vol. 9, pp. 902-913.

Nathan DM et al,Intensive Diabetes Treatment and Cardiovascular Disease in Patients with Type 1 Diabetes,The new england journal of medicine, 2005, vol. 353, No. 25, pp. 2643-2653.

Nathan DM et al.Management of Hyperglycemia in Type 2 Diabetes: A Consensus Algorithm for the Initiation and Adjustment of Therapy: Update regarding thiazolidinediones: a consensus statement from the American Diabetes Association and the European Association for the Study of Diabetes. Diabetes Care, 2008, vol. 31, No. 1, pp. 173-175.

Nathan DM et al.The Effect of Intensive Treatment of Diabetes on the Development and Progression of Long-Term Complications in Insulin-Dependent Diabetes Mellitus, the Diabetes Control and Complications Trial Research Group, The New England Journal of medicine, 1993, vol. 329, No. 14, pp. 977-986.

Norris SL, et al. Self-management education for adults with type 2 diabetes: a meta-analysis on the effect of glycemic control. Diabetes Care, 2002, vol. 25, No. 7, pp. 1159-1171.

Ohkubo Y et al. Intensive insulin therapy prevents the progression of diabetic microvascular complications in Japanese patients with non-insulin-dependent diabetes mellitus: a randomized prospective 6-year study, Diabetes Research and Clinical Practice, 1995, vol. 28, No. 2 pp. 103-117.

Peyrot M, et al. Factors associated with injection omission/non-adherence in the Global Attitudes of Patients and Physicians in Insulin Therapy Study. Diabetes Obesity and Metabolism, Dec. 2012, vol. 14, pp. 1081-1087.

Peyrot M, et al.. Insulin adherence behaviours and barriers in the multinational Global Attitudes of Patients and Physicians in insulin therapy study. Diabetic Medcine, Jan. 2012, vol. 29, No. 5, pp. 682-689.

Philis-Tsimikas A et al.: Insulin degludec once-daily in type 2 diabetes:; Simple or step-wise titration (BEGIN: Once Simple Use), Advances in Therapy, Jun. 2013, vol. 30, No. 6, pp. 607-622.

Sakharova O V et al.Effects on post-prandial glucose and AGE precursors from two initial insulin strategies in patients with Type 2 diabetes uncontrolled by oral agents, Journal of Diabetes and Its Complications, Mar. 2012, vol. 26, No. 4, pp. 333-338.

Schnell O, et al. Consensus statement on self-monitoring of blood glucose in diabetes. Diabetes, Stoffwechsel und Herz, Jul. 2009, vol. 4, pp. 285-289.

Selvin E et al.,.Meta-Analysis: Glycosylated Hemoglobin and Cardiovascular Disease in; Diabetes Mellitus, Annals of Internal medicine,2004, vol. 141, pp. 421-431.

The ADVANCE Collaborative Group, Patel A et al.Intensive Blood Glucose Control and Vascular Outcomes in Patients with Type 2 Diabetes, The new England Journal of Medicine, 2008, vol. 358, pp. 2560-2572.

UK Prospective Diabetes Study (UKPDS) Group, Intensive blood-glucose control with sulphonylureas or insulin compared with conventional treatment and risk of complications in patients with type 2 diabetes (UKPDS 33)., Lancet, 1998, vol. 352 (9131), pp. 837-853.

Yeaw J, et al. Cost of self-monitoring of blood glucose in Canada among patients on an insulin regimen for diabetes. Diabetes Therapeutics . Epub ,2012 vol. 3, No. 7, pp. 1-17 doi: 10.1007/s13300-012-0007-6.

Yeaw J, et al., Self-monitoring blood glucose test strip utilization in Canada, Diabetes, Jun. 2012, vol. 61(Suppl 1), p. A35.

Yeaw J, et al.. Cost of self-monitoring of blood glucose in the United States among patients on an insulin regimen for diabetes. Journal of Managed Care Pharmacy, Jan./Feb. 2012, vol. 18, No. 1, pp. 21-32.

American Diabetes Association. Insulin administration. Diabetes Care. 2002 vol. 25: pp. S112-S115.

Heise T, et al.. Insulin degludec: four times lower pharmacodynamic variability than insulin glargine under steady-state conditions in type 1 diabetes. Diabetes Obesity and Metabolism Sep. 2012, vol. 14, pp. 859-864.

Heise T, et al. Insulin degludec 200 U/mL is ultra-long-acting and has a flat and stable glucose-lowering effect. Diabetes, Jun. 2012, vol. 61(Suppl. 1) p. A91.

World Medical Association. World Medical Association Declaration of Helsinki: Ethical principles for medical research involving human subjects—Last amended by the 59th WMA General Assembly, Seoul. 2008. Available at: http://www.wma.net/en/30publications/10policies/b3/17c.pdf. Accessed Sep. 14, 2015.

International Conference on Harmonisation. ICH Harmonised Tripartite Guideline:Guideline for Good Clinical Practice. E6 (R1), Step 4. 1996. Available at: http://www.ich.org/fileadmin/Public_Web_Site/ICH_Products/Guidelines/Efficacy/E6_R1/Step4/E6_R1_Guideline.pdf. Accessed Sep. 14, 2015.

Niskanen L, et al. Randomized, multinational, open-label, 2-period, crossover comparison of biphasic insulin aspart 30 and biphasic insulin lispro 25 and pen devices in adult patients with type 2 diabetes mellitus. Clinical Therapeutics 2004, vol. 26 pp. 531-540.

Garg S, et al. Preference for a new prefilled insulin pen compared with the original pen. Current Medical Research & Opinion, Oct. 2011, vol. 27, pp. 2323-2333.

Garber AJ, et al; on behalf of the NN1250-3582 BEGINTM BB T2D trial investigators. Insulin degludec, an ultra-long acting basal insulin, versus insulin glargine in basal-bolus treatment with meal-time insulin aspart in type 2 diabetes (BEGINTM Basal-Bolus Type 2): a phase 3, randomised, open-label, treat-to-target non-inferiority trial. Lancet, Apr. 2012, vol. 379, pp. 1498-1507.

Zinman B, et al; on behalf of the NN1250-3579 BEGIN tm Once Long trial investigators. Insulin degludec versus insulin glargine in insulin-naïve patients with type 2 diabetes: a 1-year, randomized, treat-to-target trial (BEGIN tm Once Long). Diabetes Care, Dec. 2012, vol. 35, pp. 2464-2471.

Bergenstal R, Bhargava A, Jain RK, et al; on behalf of the NN1250-3672 BEGIN TM Low Volume trial investigators. 200 U/ml insulin degludec improves glycemic control similar to insulin glargine with a low risk of hypoglycemia in insulin-naïve people with type 2 diabetes. Abstract 207. http://am.aace.com/2012/sites/all/files/abstract-061812.pdf. Accessed Jan. 19, 2013.

Onishi Y, et al. Superior glycaemic control with once daily insulin degludec/ insulin aspart versus insulin glargine in Japanese adults with type 2 diabetes inadequately controlled on oral drugs: a randomized, controlled phase 3 trial. Diabetes Obesity and Metabolism, Sep. 2013, vol. 15, pp. 826-832.

Rakel RE. Improving patient acceptance and adherence in diabetes management: a focus on insulin therapy. Advances in Therapy, Sep. 2009, vol. 26, pp. 838-846.

Ross SA, et al. Barriers to effective insulin treatment: the persistence of poor glycemic control in type 2 diabetes. Current Medical Research and Opinion, Sep. 2011, vol. 27(Suppl 3), pp. 13-20.

Reimer T, et al. Intuitiveness, instruction time, and patient acceptance of a prefilled insulin delivery device and a reusable insulin delivery device in a randomized, open-label, crossover handling study in patients with type 2 diabetes. Clinical Therapeutics. 2008, vol. 30, pp. 2252-2262.

Rubin RR et al.. Factors affecting use of insulin pens by patients with type 2 diabetes. Diabetes Care. 2008 vol. 31 pp. 430-432.

(56) References Cited

OTHER PUBLICATIONS

Peyrot M and Rubin RR. Factors associated with persistence and resumption of insulin pen use for patients with type 2 diabetes. Diabetes Technology & Therapeutics, Jan. 2011, vol. 13, No. 1, pp. 43-48.
Oyer D, et al. Ease of use and preference of a new versus widely available pre-filled insulin pen assessed by people with diabetes, physicians and nurses. Expert Opinion on Drug Delivery, Sep. 2011, vol. 8, pp. 1259-1269.
Bailey T, et al Usability and preference evaluation of a prefilled insulin pen with a novel injection mechanism by people with diabetes and healthcare professionals. Current Medical Research and Opinion, Sep. 2011, vol. 27, pp. 2043-2052.
Nadeau DA, et al. Healthcare professional and patient assessment of a new prefilled insulin pen versus two widely available prefilled insulin pens for ease of use, teaching and learning. Current Medical Research and Opinion, 2012, vol. 28, No. 1, pp. 3-13, published online Dec. 2011.

—◇— A. Tresiba® U100 5Zn/6ins 16p/16c
----△---- B. Tresiba® U200 5.5Zn/6ins 16p/16c
······▽······ C. Insulin degludec U500 5Zn/6ins 19p/19c
----○---- D. Insulin degludec U500 3.7Zn/6ins 60p
—□— E. Insulin degludec U500 4.3Zn/6ins 60p
----○---- F. Insulin degludec U500 5Zn/6ins 60p
······×······ G. Insulin degludec U500 5Zn/6ins 60p 204NA
----+---- H. Insulin degludec U500 5Zn/6ins 60p 6Ci

Fig. 2

1. Insulin degludec U200 5.5Zn/6ins 16p/16c
2. Insulin degludec U500 5.5zn/6ins 19p/19c
3. Insulin degludec U500 5.5zn/6ins 19p/19c 6Ci
4. Insulin degludec U500 5.5zn/6ins 19p/19c 20Ci
5. Insulin degludec U500 5.5zn/6ins 19p/19c 211NA
6. Insulin degludec U500 5.5zn/6ins 19p/19c 6Ci 211NA
7. Insulin degludec U500 5.5zn/6ins 19p/19c 20Ci 161NA
8. Insulin degludec U500 5.5zn/6ins 19p/19c 0.1trep

Fig. 3

1. Insulin degludec U200 5.5Zn/6ins 16p/16c
2. Insulin degludec U500 5.5zn/6ins 19p/19c
6. Insulin degludec U500 5.5zn/6ins 19p/19c 6Ci 211NA
7. Insulin degludec U500 5.5zn/6ins 19p/19c 20Ci 161NA

Fig. 4

HIGH CONCENTRATION INSULIN FORMULATION

CROSS-REFERENCE TO RELATED APPLICATIONS

This application is a 35 U.S.C. § 371 National Stage application of International Application PCT/EP2020/069512 (WO2021009027), filed Jul. 10, 2020, which claims priority to European Patent Application 19185958.6, filed Jul. 12, 2019.

FIELD OF THE INVENTION

The present invention relates to the field of pharmaceutical compositions of acylated insulin, and method for using such compositions in the treatment of diseases. Also, the present invention relates to the field of manufacture of such pharmaceutical compositions.

BACKGROUND OF THE INVENTION

Currently, the treatment of diabetes, both type 1 diabetes and type 2 diabetes, relies to an increasing extent on the so-called intensive insulin treatment. According to this regimen, the patients are treated with multiple daily insulin injections comprising one or two daily injections of a long acting insulin to cover the basal insulin requirement supplemented by bolus injections of a rapid acting insulin to cover the insulin requirement related to meals.

Long acting insulin compositions are well known in the art. Thus, one main type of long acting insulin compositions comprises injectable aqueous suspensions of insulin crystals or amorphous insulin. In these compositions, the insulin compounds utilized typically are protamine insulin, zinc insulin or protamine zinc insulin. Other long acting insulin compositions are e.g. Lantus® and Tresiba® having protracted profiles of action as compared to human insulin.

Crystallized insulin whether this being protamine crystallized when injecting it or whether the insulin composition crystallizes upon injection do have a number of drawbacks such as potential immunogenic reactions, homogeneity, tissue irritation and reactions and the like.

Another type of long acting insulin composition is solutions having a pH value below physiological pH from which the insulin will precipitate because of the rise in the pH value when the solution is injected. A drawback with these solutions is that the particle size distribution of the precipitate formed in the tissue on injection, and thus the release profile of the medication, depends on the blood flow at the injection site and other parameters in a somewhat unpredictable manner. A further drawback is that the solid particles of the insulin may act as a local irritant causing inflammation of the tissue at the site of injection.

Insulin is a 51 amino acid peptide hormone produced in the islets of Langerhans in the pancreas. Its primary function, acting as a monomer, is to facilitate the transport of glucose molecules across the cell membranes of adipose and muscle tissue by binding to and activating a transmembrane receptor.

A distinctive property of insulin is its ability to associate into hexamers, in which form the hormone is protected from chemical and physical degradation during biosynthesis and storage. X-ray crystallographic studies on insulin show that the hexamer consists of three dimers related by a 3-fold axis of rotation. These dimers are closely associated through the interaction of two zinc ions at its core positioned on the 3-fold axis.

When human insulin is injected into the subcutis in the form of a high-concentration pharmaceutical formulation it is self-associated, and here dissociation into monomers is relatively slow. Hexamers and dimers of insulin are slower to penetrate capillary wall than monomers.

Zinc and phenolic additives are regularly used in therapeutic insulin preparations to promote hexamer formation as a precaution against degradation during storage. In this form, however, the action of injected insulin is delayed while the hexamers diffuse through the subcutis and dissociate into dimers and monomers.

The strength of insulin formulations is described in units (U) where one unit corresponds to 0.035 mg human insulin. Hence, a 100 U/ml human insulin formulation has a concentration of 3.5 mg/ml human insulin. Insulin degludec (NεB29-hexadecandioyl-γ-Glu-(desB30) human insulin) is commercially available as a 100 U/ml product as well as a 200 U/ml product.

Formulations of insulin are usually prepared by dissolving insulin in a small volume of water under acidic conditions. Zinc is then added to the formulation followed by a neutralisation and addition of preservatives like phenol and m-cresol. Concentrated insulin formulations, however, tend to be unstable upon storage and use, and just as important the PK profile changes with the insulin concentration.

WO2008/132224 discloses pharmaceutical composition comprising spray-dried insulin to make highly concentration insulin solutions for the treatment of diabetes.

WO2007/074133 discloses pharmaceutical composition comprising insulin degludec.

It is advantageous to have concentrated insulin formulations which are stable during storage and use. Such concentrated formulations would require less frequent change of disposable injection pen, and less frequent change of cartridge in durable injection devices. Also, the substantial development within injection devices in many cases require insulin compositions which are highly concentrated.

When the insulin concentration in insulin formulations is increased, there is a general tendency for the pharmacokinetic profile to be altered. More specifically, for a given dose of the insulin, the Cmax and AUC (bioavailability) tend to decrease when the insulin concentration in the formulation is increased. The change of pharmacokinetic properties when scaling the insulin concentration is a challenge to insulin products which typically go into different administration devices where different insulin concentrations are desired.

The present invention is related to certain pharmaceutical compositions of NεB29-hexadecandioyl-γ-Glu-(desB30) human insulin which solves the problems of the prior art.

SUMMARY OF THE INVENTION

It has surprisingly been found that high concentration, soluble insulin formulations can be made which have a PK profile substantially similar to a corresponding regular U200 product, while still being stable during storage and in-use.

Hence, in a first aspect the present invention provides a soluble insulin preparation comprising:
NεB29-hexadecandioyl-γ-Glu-(desB30) human insulin in a concentration from 1800 nmol/ml to 4200 nmol/ml,
Zinc ions in a concentration from 4.0 Zn/6Ins to 7.0 Zn/6Ins, Niacinamide in a concentration from 110 mM to 220 mM or treprostinil in a concentration from 0.02 μg/ml to 1 μg/ml, Citrate in a concentration from 6 mM to 40 mM, and pH in the range from 7.0 to 8.0.

In a first embodiment of the invention the concentration of said zinc ions is from 5.0 Zn/6Ins to 5.5 Zn/6Ins.

In another embodiment of the invention the concentration of said zinc ions is from 5.0 Zn/6Ins to 6.0 Zn/6Ins.

In another embodiment the soluble insulin preparation comprises niacinamide in a concentration from 110 mM to 220 mM.

In another embodiment the soluble insulin preparation has a pH in the range from 7.4 to 7.8.

In another embodiment the soluble insulin preparations further comprise a phenolic preservative or a mixture of phenolic preservatives.

In another embodiment said phenolic preservative or mixture of phenolic preservatives is a mixture of phenol and m-cresol.

In another aspect the present invention provides a method of reducing the blood glucose level in a mammal by administering to a subject in need of such treatment a therapeutically effective dose of a soluble insulin preparation according to the present invention.

With the present invention it is possible for a person with diabetes to switch between e.g. a U200 formulation and a U500 formulation of NεB29-hexadecandioyl-γ-Glu-(desB30) human insulin without adjusting the dose.

It is also now possible for an individual who need very high doses of basal insulin, e.g. in excess of 160 U/day, to achieve this with a single daily dose.

Furthermore, since a typical insulin pen or cartridge typically contains 3 mL, there will be much more than 600 U in a single pen or cartridge, e.g. 1500 U for a U500 product, which means that the pen or cartridge need replacement less frequently. Also, the person will not as often have to split the dose when the pen or cartridge is nearly used up.

DESCRIPTION OF THE INVENTION

In a first aspect the present invention provides a soluble insulin preparation comprising:
NεB29-hexadecandioyl-γ-Glu-(desB30) human insulin in a concentration from 1800 nmol/ml to 4200 nmol/ml,
Zinc ions in a concentration from 4.0 Zn/6Ins to 7.0 Zn/6Ins,
Niacinamide in a concentration from 110 mM to 220 mM or treprostinil in a concentration from 0.02 μg/ml to 1 μg/ml,
Citrate in a concentration from 6 mM to 40 mM, and pH in the range from 7.0 to 8.0.

In another aspect the present invention relates to a soluble insulin preparation comprising:
NεB29-hexadecandioyl-γ-Glu-(desB30) human insulin in a concentration of 3000 nmol/ml,
Zinc ions in a concentration of 5.5 Zn/6Ins,
Niacinamide in a concentration of 211 mM,
citrate in a concentration of 6 mM, and pH of 7.6.

In another aspect the present invention relates to a soluble insulin preparation comprising:
NεB29-hexadecandioyl-γ-Glu-(desB30) human insulin in a concentration of 3000 nmol/ml,
Zinc ions in a concentration of 5.5 Zn/6Ins,
Niacinamide in a concentration of 161 mM,
citrate in a concentration of 20 mM, and pH of 7.6.

For insulin preparations the concentration of insulin is typically given in units per milliliter, U/mL For NεB29-hexadecandioyl-γ-Glu-(desB30) human insulin 100 units (100 U) is the equivalent of 3.66 mg or 600 nmol of NεB29-hexadecandioyl-γ-Glu-(desB30) human.

It is also typical for insulin preparation comprising zinc to state the zinc concentration relative to the concentration of insulin calculated as hexamers, i.e. insulin concentration divided by 6. This molar ratio is termed "Zn/6Ins", i.e. describing the relative molar concentration of zinc to one sixth of the insulin concentration.

When the insulin concentration in insulin formulations is increased, there is a general tendency for the pharmacokinetic profile to be altered. More specifically, for a given dose of the insulin, the Cmax and AUC (bioavailability) tend to decrease when the insulin concentration in the formulation is increased. This means that the glucose lowering effect of a U500 formulation will be less than that of a U200 formulation even though the same amount of insulin is administered. Hence, the two formulations will therefore not be bioequivalent.

This lack of scalability is a challenge for insulin preparations since insulins go into several different administration devices for which different concentrations of insulin is highly desirable.

The present inventors have found that for soluble preparations of NεB29-hexadecandioyl-γ-Glu-(desB30) human insulin the addition of citrate and niacinamide causes in increase of Cmax and AUC (bioavailability), thereby making it possible to make highly concentrated for-mutation of NεB29-hexadecandioyl-γ-Glu-(desB30) human insulin which is bioequivalent with a U200 preparation of the same insulin. The same observation has been made with the addition of treprostinil.

The soluble insulin preparation comprises NεB29-hexadecandioyl-γ-Glu-(desB30) human insulin in a concentration from 1800 nmol/ml to 4200 nmol/ml. In some embodiments the concentration of said NεB29-hexadecandioyl-γ-Glu-(desB30) human insulin is from 2400 nmol/ml to 3600 nmol/ml or from 2700 nmol/ml to 3300 nmol/ml. In another embodiment the concentration of NεB29-hexadecandioyl-γ-Glu-(desB30) human insulin is about 3000 nmol/ml.

The term "about" as used herein is intended to mean plus or minus 10%, such as plus or minus 5%. Hence, the term "about 100 U" is from 90 U to 110 U.

The soluble insulin preparation comprises zinc which may be added as e.g. zinc acetate or zinc chloride. The soluble preparations may comprise zinc ions in the range from 4.0 Zn/6Ins to 7.0 Zn/6Ins. In one embodiment the concentration of said zinc ions is from 4.0 Zn/6Ins to 6.0 Zn/6Ins. In another embodiment the concentration of said zinc ions is from 4.7 Zn/6Ins to 5.7 Zn/6Ins. In another embodiment the concentration of said zinc ions is from 5.0 Zn/6Ins to 6.0

Zn/6Ins. In yet another embodiment the concentration of said zinc ions is from 5.0 Zn/6Ins to 5.5 Zn/6Ins. In another embodiment the soluble insulin preparation according to the invention has a concentration of zinc ions of 5.0 Zn/6Ins. In another embodiment the soluble insulin preparation according to the invention has a concentration of zinc ions of 5.5 Zn/6Ins. In another embodiment the soluble insulin preparation according to the invention has a concentration of zinc ions of 6.0 Zn/6Ins.

The soluble insulin preparation according to the invention comprises niacinamide in a concentration from 110 mM to 220 mM or treprostinil in a concentration from 0.02 µg/ml to 1 µg/ml. In one embodiment the soluble insulin preparation comprises niacinamide. The soluble insulin preparation may in an embodiment comprises niacinamide in a concentration from 135 mM to 195 mM, or from 150 mM to 180 mM. In another embodiment the soluble preparation comprises niacinamide in a concentration from 110 mM to 140 mM, or from 190 mM to 220 mM. In another embodiment the soluble preparation comprises niacinamide in a concentration from 110 mM to 170 mM. In another embodiment the soluble preparation comprises niacinamide in a concentration from 150 mM to 220 mM.

In another embodiment the soluble preparation comprises niacinamide in a concentration of about 160 mM. In another embodiment the soluble preparation comprises niacinamide in a concentration of 161 mM. In another embodiment the soluble preparation comprises niacinamide in a concentration of about 200 nM. In another embodiment the soluble preparation comprises niacinamide in a concentration of 204 mM. In another embodiment the soluble preparation comprises niacinamide in a concentration of about 210 nM. In another embodiment the soluble preparation comprises niacinamide in a concentration of 211 mM.

In another embodiment the soluble insulin preparation comprises treprostinil. In another embodiment the soluble insulin preparation comprises treprostinil in a concentration from 0.02 µg/ml to 0.5 µg/ml, from 0.04 µg/ml to 0.3 µg/ml, from 0.05 µg/ml to 0.2 µg/ml or from 0.1 to 1 µg/ml. In another embodiment the soluble insulin preparation comprises treprostinil in a concentration of 0.1 µg/ml.

The soluble insulin preparation as described herein comprises citrate in a concentration from 6 mM to 40 mM. The term citrate is to be understood to include citrate salt as well as citric acid. In one embodiment the soluble insulin preparations comprises citrate in a concentration from 15 mM to 30 mM, from 6 mM to 20 mM or from 20 mM to 40 mM. The soluble insulin preparation as described herein comprises citrate in a concentration of 6 mM. The soluble insulin preparation as described herein comprises citrate in a concentration of 10 mM. The soluble insulin preparation as described herein comprises citrate in a concentration of 20 mM.

The soluble insulin preparations of the present invention have a pH in the range from 7.0 to 8.0. In one embodiment the pH is from 7.2 to 8.0, from 7.4 to 7.8, from 7.0 to 7.5, from 7.4 to 8.0 or from 7.4 to 7.8. In another embodiment the pH of the soluble insulin preparation is pH 7.6.

Since soluble insulin preparations are sterile liquids they may comprise a preservative or they may be free from any preservative. In one embodiment the soluble insulin preparation according to the invention further comprising a phenolic preservative or a mixture of phenolic preservatives. In one embodiment said phenolic preservative is phenol. In another embodiment said preservative is a mixture of phenolic preservatives, such as a mixture of phenol and m-cresol. In another embodiment the preservative is a mixture of phenol and m-cresol and the concentration of phenol is from 1.3 mg/ml to 2.0 mg/ml and the concentration of m-cresol is from 1.5 mg/ml to 2.3 mg/ml. In another embodiment the preservative is a mixture of phenol and m-cresol and the concentration of phenol is 1.8 mg/ml and the concentration of m-cresol is 2.05 mg/ml.

In some embodiments the soluble insulin preparation comprises a further isotonicity agent. In one embodiment said isotonicity agent is glycerol. The need for the addition of such an isotonicity agent will be apparent when the concentrations of the other constituents of the soluble insulin preparation are determined. In another embodiment the soluble insulin preparation comprises no further isotonicity agent.

In one embodiment the soluble insulin preparation comprises no further buffering agent.

In an aspect the invention is provided a method of reducing the blood glucose level in a mammal by administering to a subject in need of such treatment a therapeutically effective dose of a soluble insulin preparation as described herein.

In an aspect the invention is provided a method for the treatment of diabetes mellitus in a subject comprising administering to said subject a soluble insulin preparation as described herein.

In another aspect is provided a soluble insulin preparation for use in the treatment or prevention of hyperglycemia including stress induced hyperglycemia, type 2 diabetes, impaired glucose tolerance, type 1 diabetes, and burns, operation wounds and other diseases or injuries where an anabolic effect is needed, myocardial infarction, stroke, coronary heart disease and other cardiovascular disorders and treatment of critically ill diabetic and non-diabetic patients.

The insulin preparations of the invention may be prepared as is known in the art, e.g. as described in the Examples.

The invention will be summarized in the following embodiments:

1. A soluble insulin preparation comprising:
   NεB29-hexadecandioyl-γ-Glu-(desB30) human insulin in a concentration from 1800 nmol/ml to 4200 nmol/ml,
   Zinc ions in a concentration from 4.0 Zn/6Ins to 7.0 Zn/6Ins,
   Niacinamide in a concentration from 110 mM to 220 mM or treprostinil in a concentration from 0.02 µg/ml to 1 µg/ml,
   Citrate in a concentration from 6 mM to 40 mM, and
   pH in the range from 7.0 to 8.0.
2. The soluble insulin preparation according embodiment 1, wherein the concentration of said NεB29-hexadecandioyl-γ-Glu-(desB30) human insulin is from 2400 nmol/ml to 3600 nmol/ml.
3. The soluble insulin preparation according to any of the preceding embodiments, wherein the concentration of said NεB29-hexadecandioyl-γ-Glu-(desB30) human insulin is from 2700 nmol/ml to 3300 nmol/ml.
4. The soluble insulin preparation according to any of the preceding embodiments, wherein the concentration of said NεB29-hexadecandioyl-γ-Glu-(desB30) human insulin is about 3000 nmol/ml.
5. The soluble insulin preparation according to any of the preceding embodiments, wherein the concentration of said zinc ions is from 5.0 Zn/6Ins to 6.5 Zn/6Ins.
6. The soluble insulin preparation according to any of the preceding embodiments, wherein the concentration of said zinc ions is from 5.0 Zn/6Ins to 6.0 Zn/6Ins.

7. The soluble insulin preparation according to any of the preceding embodiments, wherein the concentration of said zinc ions is from 4.7 Zn/6Ins to 5.7 Zn/6Ins.
8. The soluble insulin preparation according to any of the preceding embodiments, wherein the concentration of said zinc ions is 5.0 Zn/6Ins or 5.5 Zn/6Ins.
9. The soluble insulin preparation according to any of the preceding embodiments, which comprises niacinamide.
10. The soluble insulin preparation according to any of the preceding embodiments, which comprises niacinamide in a concentration from 135 mM to 195 mM, or from 150 mM to 180 mM.
11. The soluble insulin preparation according to any of the preceding embodiments, which comprises niacinamide in a concentration from 110 mM to 140 mM, or from 190 mM to 220 mM.
12. The soluble insulin preparation according to any of the preceding embodiments, which comprises niacinamide in a concentration from 150 mM to 220 mM.
13. The soluble insulin preparation according to any of the preceding embodiments, which comprises niacinamide in a concentration from 110 mM to 170 mM.
14. The soluble insulin preparation according to any of embodiments 1-8, which comprises treprostinil.
15. The soluble insulin preparation according to embodiment 14, which comprises treprostinil in a concentration from 0.02 μg/ml to 0.5 μg/ml, from 0.04 μg/ml to 0.3 μg/ml, from 0.05 μg/ml to 0.2 μg/m or from 0.1 to 1 μg/ml.
16. The soluble insulin preparation according to any of the preceding embodiments, which comprises citrate in a concentration from 15 mM to 30 mM, from 6 mM to 20 mM or from 20 mM to 40 mM.
17. The soluble insulin preparation according to any of the preceding embodiments, which comprises citrate in a concentration of 6 mM.
18. The soluble insulin preparation according to any of the preceding embodiments, which comprises citrate in a concentration of 10 mM.
19. The soluble insulin preparation according to any of the preceding embodiments, which comprises citrate in a concentration of 20 mM.
20. The soluble insulin preparation according to any of the preceding embodiments, which has a pH from 7.2 to 8.0, from 7.4 to 7.8, from 7.0 to 7.5, from 7.4 to 8.0 or from 7.4 to 7.8.
21. The soluble insulin preparation according to embodiment 20, which has pH 7.6.
22. The soluble insulin preparation according to any of the preceding embodiments further comprising a phenolic preservative or a mixture of phenolic preservatives.
23. The soluble insulin preparation according to embodiment 22 wherein said phenolic preservative is phenol.
24. The soluble insulin preparation according to embodiment 22 wherein said mixture of phenolic preservatives is phenol and m-cresol.
25. The soluble insulin preparation according to embodiment 23, wherein the concentration of phenol is from 1.3 mg/ml to 2.0 mg/ml and the concentration of m-cresol is from 1.5 mg/ml to 2.3 mg/ml.
26. The soluble insulin preparation according to embodiment 25, wherein the concentration of phenol is 1.8 mg/ml and the concentration of m-cresol is 2.05 mg/ml.
27. The soluble insulin preparation according to any of the preceding embodiments, which comprises a further isotonicity agent.
28. The soluble insulin preparation according to embodiment 27, wherein said isotonicity agent is glycerol.
29. The soluble insulin preparation according to any of embodiments 1-26, which comprises no further isotonicity agent.
30. The soluble insulin preparation according to any of the preceding embodiments, which comprises no further buffering agent.
31. The soluble insulin preparation according to embodiment 1, comprising:
    NεB29-hexadecandioyl-γ-Glu-(desB30) human insulin in a concentration of 3000 nmol/ml,
    Zinc ions in a concentration of 5.5 Zn/6Ins,
    Niacinamide in a concentration of 211 mM,
    citrate in a concentration of 6 mM, and pH of 7.6.
32. The soluble insulin preparation according to embodiment 1, comprising:
    NεB29-hexadecandioyl-γ-Glu-(desB30) human insulin in a concentration of 3000 nmol/ml,
    Zinc ions in a concentration of 5.5 Zn/6Ins,
    Niacinamide in a concentration of 161 mM,
    citrate in a concentration of 20 mM, and pH of 7.6.
33. A method of reducing the blood glucose level in a mammal by administering to a subject in need of such treatment a therapeutically effective dose of a soluble insulin preparation according to any of the preceding embodiments.
34. A method for the treatment of diabetes mellitus in a subject comprising administering to said subject a soluble insulin preparation according to any one of embodiments 1-32.
35. A soluble insulin preparation according to any one of embodiments 1-32, for use in the treatment or prevention of hyperglycemia including stress induced hyperglycemia, type 2 diabetes, impaired glucose tolerance, type 1 diabetes, and burns, operation wounds and other diseases or injuries where an anabolic effect is needed, myocardial infarction, stroke, coronary heart disease and other cardiovascular disorders and treatment of critically ill diabetic and non-diabetic patients.

EXAMPLES

Example 1—Formulation for Pig Study

The aim of this study was to compare Tresiba® U100, Tresiba® U200 and a similar formulation of degludec at 3000 nmol/L (U500), evaluate the effect of replacing the combination of phenol and m-cresol by phenol only, evaluate the effect of reducing relative zinc concentration (Zn/6Ins), evaluate the effect of adding niacinamide, and furthermore evaluate effect of adding citrate by a pig study. Beforehand the formulations should be tested for physical and chemical stability by an in use test and storage.

Insulin degludec was added to water to about 8 mM and dissolved. pH was adjusted by 0.2N NaOH to pH 7.6 and the stock solution was sterile filtered and content was determined. To insulin degludec stock solution were added in mentioned order excess of water, glycerol (20% (w/vol)), phenol (500 mM), m-cresol (160 mM), niacinamide (1000 mM), trisodium citrate (100 mM), and zinc acetate (20 mM, pH ad 6.6 by hydrochloric acid). Zinc acetate was added gradually. pH was then adjusted to 7.6 by 0.2N sodium hydroxide/hydrochloric acid, volume adjusted with water and the formulation sterile filtered. The formulations were filled in 3 mL cartridge for insulin pen.

A subset of cartridges were in use tested at 30° C. for 12 weeks adding 25 μL air to 1 mL formulation in each cartridge and rotating 1 min/day. The cartridges were examined regularly by visual inspection and no change or particle formation was found for any of the for-mutations during the period. The formulations were tested for chemical stability by determination of covalent high molecular weight products (HMWP) during 12 weeks at 30° C. and all found stable and about the same low covalent dimer formation rate.

TABLE 1

Formulations

| Formulations Pig study KMRP180802 | de-gludec nmol/mL | glycerol %(w/vol) | phenol mM | m-cresol mM | zinc acetate Zn/6ins | niacinamide mM | citrate, trisodium mM | pH |
|---|---|---|---|---|---|---|---|---|
| A | 600 | 1.96 | 16 | 16 | 5 | 0 | 0 | 7.6 |
| B | 1200 | 1.96 | 16 | 16 | 5.5 | 0 | 0 | 7.6 |
| C | 3000 | 1.96 | 19 | 19 | 5 | 0 | 0 | 7.6 |
| D | 3000 | 1.71 | 60 | 0 | 3.7 | 0 | 0 | 7.6 |
| E | 3000 | 1.71 | 60 | 0 | 4.3 | 0 | 0 | 7.6 |
| F | 3000 | 1.71 | 60 | 0 | 5 | 0 | 0 | 7.6 |
| G | 3000 | 0 | 60 | 0 | 5 | 204 | 0 | 7.6 |
| H | 3000 | 1.56 | 60 | 0 | 5 | 0 | 6 | 7.6 |

Example 2—Animal Experiment, Study KMRP180802

Sixteen female domestic pigs (mean body weight approximately 80 kg) were fasted overnight prior to the studies and fed 8 hours after dosing of the test insulin formulations. To investigate different formulations of insulin degludec, each pig was to receive the formulations described in Table 1 in a balanced, non-randomized cross-over design according to the schedule outlined in Table 2.

TABLE 2

Dosing schedule for pig experiment.

| Formulations Pig study KMRP180802 | de-gludec nmol/mL | Dose Pen Units | October 1 | October 4 | October 8 | October 11 | October 15 | October 18 | October 22 | October 25 |
|---|---|---|---|---|---|---|---|---|---|---|
| A | 600 | 25 | 1, 2 | 3, 4 | 5, 6 | 7, 8 | 9, 10 | 11, 12 | 13, 14 | 15, 16 # |
| B | 1200 | 12.5 | 3, 4 | 5, 6 | 7, 8 | 9, 10 | 11, 12 | 13, 14 | 15, 16 # | 1, 2 |
| C | 3000 | 5 | 5, 6 | 7, 8 | 9, 10 | 11, 12 | 13, 14 | 15, 16 # | 1, 2 | 3, 4 |
| D | 3000 | 5 | 7, 8 | 9, 10 | 11, 12 | 13, 14 | 15, 16 | 1, 2 | 3, 4 | 5, 6* |
| E | 3000 | 5 | 9, 10 | 11*, 12 | 13, 14 | 15, 16 | 1, 2 | 3, 4 | 5, 6 | 7, 8 |
| F | 3000 | 5 | 11, 12 | 13, 14 | 15, 16 | 1, 2 | 3, 4 | 5, 6 | 7, 8 | 9, 10 |
| G | 3000 | 5 | 13, 14 | 15, 16 | 1, 2 | 3, 4 | 5, 6 | 7, 8 | 9, 10 | 11, 12 |
| H | 3000 | 5 | 15, 16 | 1, 2 | 3, 4 | 5, 6 | 7, 8 | 9, 10 | 11, 12 | 13, 14 |

*Excluded due to low exposure indicating dosing failure
Pig no. 16 replaced by new pig on these days One pig had to be replaced during the study, so in total 17 pigs were studied.

Figure 1A:
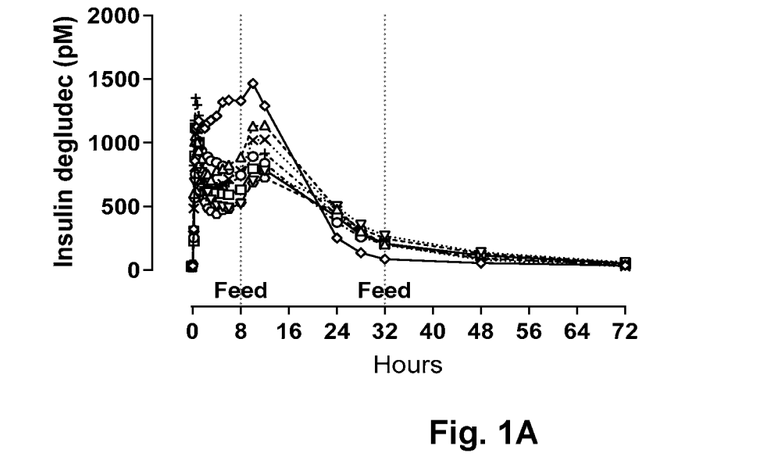
FIG. 1A. PK profiles of insulin degludec obtained with the test formulations A-H data to 72 hours (mean).

Pigs were dosed in the morning and samples were drawn as indicated in FIG. 1 for measurement of insulin degludec using a specific luminescent oxygen channeling immunoassay utilizing two antibodies.

Data analysis was performed on AUCs derived by non-compartmental analysis (Phoenix software) and since formulations differed slightly from the intended concentration, dose-normalized AUCs (AUC/dose) were calculated.

Results

Comparison of formulations A and B illustrates that the PK curve for formulation B is flatter than that of the U100 formulation, but the total dose normalized AUCs do not differ appreciably (FIG. 1A and table 3). Formulation B contained 5.5 Zn/6 insulin molecules (like Tresiba® U200), while formulation A contained 5 Zn/6 insulin molecules (like Tresiba® U100). By increasing the insulin concentration to 3000 nmol/ml in formulation C with 5 Zn/6 insulin molecules, a further flattening of the PK curve is observed but now a decrease in bioavailability of about 18% relative to formulation A and B is apparent (FIG. 1A and table 3). This relatively large reduction illustrates that it will be difficult to make a 3000 nmol/ml formulation of insulin degludec bioequivalent to a 1200 nmol/ml formulation and that higher doses of a U500 formulation compared to a U200 formulation would be needed to give equivalent glucose lowering effects. Changing from 19 mM phenol and 19 mM m-cresol to 60 mM phenol and 0 mM m-cresol did not further affect the PK profile (reduction in AUC/dose approximately 20% vs formulation B), but reduction in Zn partially increased the bioavailability and adding either citrate or niacinamide more strongly increased the bioavailability relative to formulations A and B. For formulations G and H, the reduction in AUC compared to formulation B was less than seen with formulation F, being only 10% for formulation G and only 2% for formulation H.

Figure 1B:
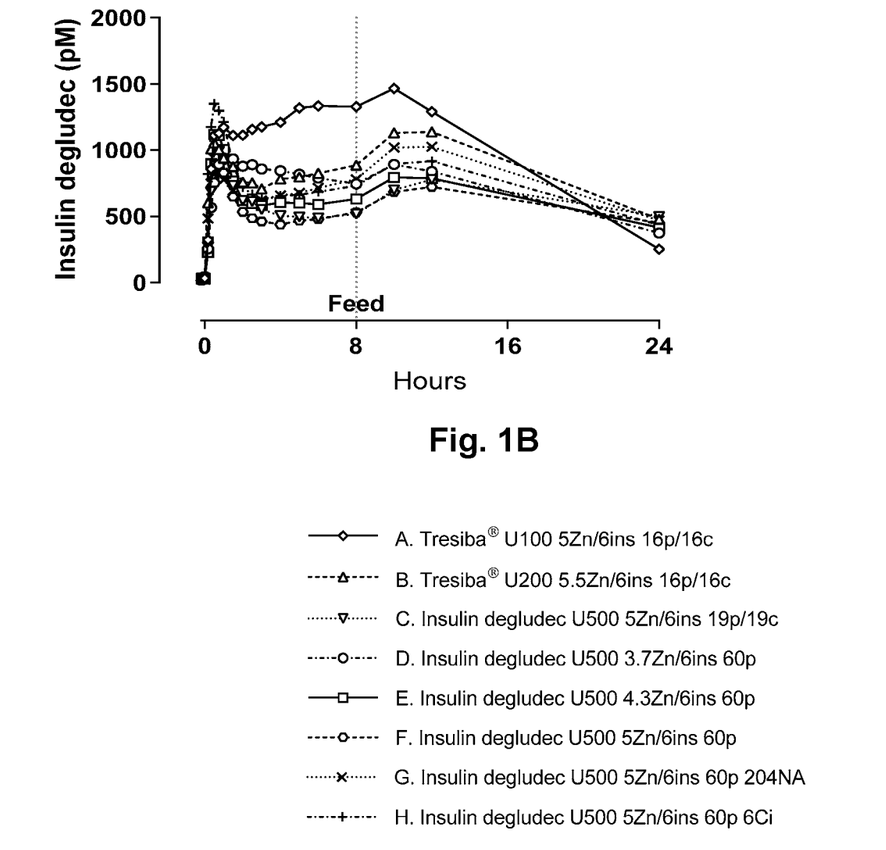
FIG. 1B. PK profiles of insulin degludec obtained with the test formulations A-H data to 24 hours (mean±SEM).
Figure 2:
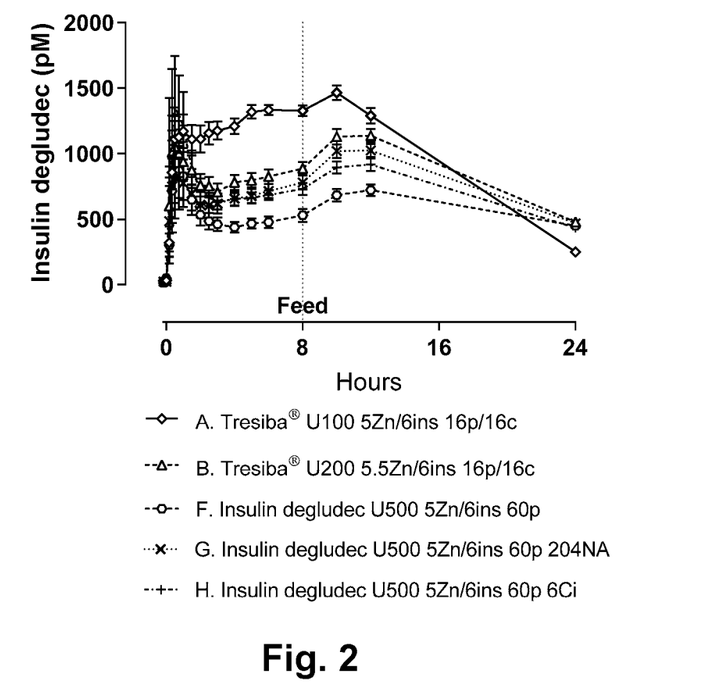
FIG. 2. PK profiles of insulin degludec obtained with the test formulations A, B, F, G and H data to 24 hours.

Pigs exhibit an early peak in absorption of insulin degludec that is not seen in humans. The estimation and comparison of Cmax is therefore associated with uncertainty. Considering the second peak (maximal exposure that occurs around 10-12 hours after dosing), we observed that the reduction in formulation F is approximately 38% to that of formulation B. Cmax was increased in formulation G (only 10% reduction compared to formulation B) and in formulation H (only 21% reduction compared to formulation B). These differences can be seen in FIG. 1B and FIG. 2. For clarity, FIG. 1B shows all mean data plotted to 24 hours only and FIG. 2 shows the data for formulations A, B, F, G and H only with data plotted to 24 hours.

TABLE 3

Dose-normalized AUCs calculated by non-compartmental analysis

| Formulation | A | B | C | D | E | F | G | H |
|---|---|---|---|---|---|---|---|---|
| AUC/dose (mean ± SD) | 776 ± 100 | 798 ± 77 | 658 ± 166 | 690 ± 55 | 693 ± 68 | 640 ± 78 | 718 ± 68 | 783 ± 118 |
| Percent difference to B | −3% | | −18% | −14% | −13% | −20% | −10% | −2% |

Conclusion

Reduced relative bioavailability and reduced late Cmax are observed when up-concentrating insulin degludec from 1200 nmol/ml (U200) to 3000 nmol/ml (U500) to an extent that the U500 formulation is not bioequivalent to the U200 formulation and where higher doses of a U500 formulation compared to a U200 formulation would be needed to give equivalent glucose lowering effects. We have solved this problem by showing that both citrate and niacinamide almost restore the AUC and partially the Cmax and we are guided to test the combination of citrate and niacinamide to make a U500 formulation that is bioequivalent to U200 Tresiba® where the same dose of a U500 formulation and U200 Tresiba® will give equivalent glucose lowering effects.

Example 3—Formulation for Pig Study JSTU190601

The aim of this study was to compare degludec U200 and a similar formulation of degludec at 3000 nmol/L (U500), evaluate the effect of citrate at two levels, evaluate the effect of niacinamide added to isotonicity and omitting glycerol, evaluate effect of two combinations of citrate and niacinamide and finally test effect of adding treprostinil by an additional pig study. Beforehand the formulations should be tested for physical and chemical stability by an in use test and storage.

Insulin degludec was added to water to about 7 mM and dissolved. pH was adjusted by 0.2N NaOH to pH 7.8 and the stock solution was sterile filtered and content was determined. To degludec stock solution were added in mentioned order excess of water, glycerol (20% (w/vol)), phenol (500 mM), cresol (160 mM), zinc acetate (20 mM, pH ad 6.6 by hydrochloric acid, added gradually), niacinamide (1000 mM), trisodium citrate (300 mM), and treprostinil (10 µg/mL). pH was then adjusted to 7.6 by 0.2N sodium hydroxide/hydrochloric acid, volume adjusted with water and the formulation sterile filtered. The formulations were filled in 3 mL cartridge for insulin pen.

TABLE 4

Formulations

| Formulations Pig study JSTU190601 | degludec nmol/mL | glycerol %(w/vol) | phenol mM | m-cresol mM | zinc acetate Zn/6ins | niacinamide mM | citrate, trisodium mM | treprostinil µg/mL | pH |
|---|---|---|---|---|---|---|---|---|---|
| 1 | 1200 | 2.09 | 16 | 16 | 5.5 | 0 | 0 | 0 | 7.6 |
| 2 | 3000 | 1.96 | 19 | 19 | 5.5 | 0 | 0 | 0 | 7.6 |
| 3 | 3000 | 1.77 | 19 | 19 | 5.5 | 0 | 6 | 0 | 7.6 |
| 4 | 3000 | 1.33 | 19 | 19 | 5.5 | 0 | 20 | 0 | 7.6 |
| 5 | 3000 | 0 | 19 | 19 | 5.5 | 211 | 0 | 0 | 7.6 |
| 6 | 3000 | 0 | 19 | 19 | 5.5 | 211 | 6 | 0 | 7.6 |
| 7 | 3000 | 0 | 19 | 19 | 5.5 | 161 | 20 | 0 | 7.6 |
| 8 | 3000 | 1.96 | 19 | 19 | 5.5 | 0 | 0 | 0.1 | 7.6 |

Example 4—Animal Experiment

The study was performed in 16 female LYD pigs of SPF origin delivered from Lars Jonsson, Hillerødvej 70, Lynge, Denmark. At start of the acclimatization period, the body weight of the pigs was in the range of 59.5-68.5 kg, with an expected minimum weight of 70 kg on the first dosing day. Four extra animals were available during the study and three of these were included due to catheter malfunction and/or infection.

Animals were fasted overnight prior to the studies and fed 8 hours after dosing of the test insulin formulations. To investigate different formulations of insulin degludec, each pig was to receive the formulations described in Table 4 in a balanced, non-randomized cross-over design according to the schedule outlined in Table 5.

TABLE 5

Dosing schedule for experiment JStu190601

| Formulation | Batch no. | Conc nmol/ml | Dose Pen Units/nmol | 03/06 | 06/06 | 11/06 | 14/06 | 17/06 | 20/06 | 24/06 | 27/06 |
|---|---|---|---|---|---|---|---|---|---|---|---|
| 1 | 0100-0214-0454-1B | 1200 | 12.5/150 | 1, 2 | 3, 4 | 5, 6 | 7, 8 | 9, 10 | 11, 12 | 13, 14 | 15, 16 |
| 2 | 0100-0216-0454-1A | 3000 | 5/150 | 3, 4 | 5, 6 | 7, 8 | 9, 10 | 11, 12 | 13, 14 | 15, 16 | 1, 2 |
| 3 | 0100-0218-0454-1A | 3000 | 5/150 | 5, 6 | 7, 8 | 9, 10 | 11, 12 | 13, 14 | 15, 16 | 1, 2 | 3, 4 |
| 4 | 0100-0220-0454-1A | 3000 | 5/150 | 7, 8 | 9, 10 | 11, 12 | 13, 14 | 15, 16 | 1, 2 | 3, 4 | 5, 6 |
| 5 | 0100-0221-0454-1A | 3000 | 5/150 | 9, 10 | 11, 12 | 13, 14 | 15, 16 | 1, 2 | 3, 4 | 5, 6 | 7, 8 |
| 6 | 0100-0222-0454-1A | 3000 | 5/150 | 11, 12 | 13, 14 | 15, 16 | 1, 2 | 3, 4 | 5, 6 | 7, 8 | 9, 10 |
| 7 | 0100-0223-0454-1A | 3000 | 5/150 | 13, 14 | 15, 16 | 1, 2 | 3, 4 | 5, 6 | 7, 8 | 9, 10 | 11, 12 |
| 8 | 0100-0224-0454-1A | 3000 | 5/150 | 15, 16 | 1, 2 | 3, 4 | 5, 6 | 7, 8 | 9, 10 | 11, 12 | 13, 14 |

Three of the four extra animals were used to replace animals with malfunctioning catheters, so in total 19 pigs were studied. A total of seven dosings were not performed due to malfunctioning injection catheters. One animal from group 8 was omitted from the data analysis since sampling in that animal was not possible on that day beyond 150 min after insulin dosing.

Figure 3:
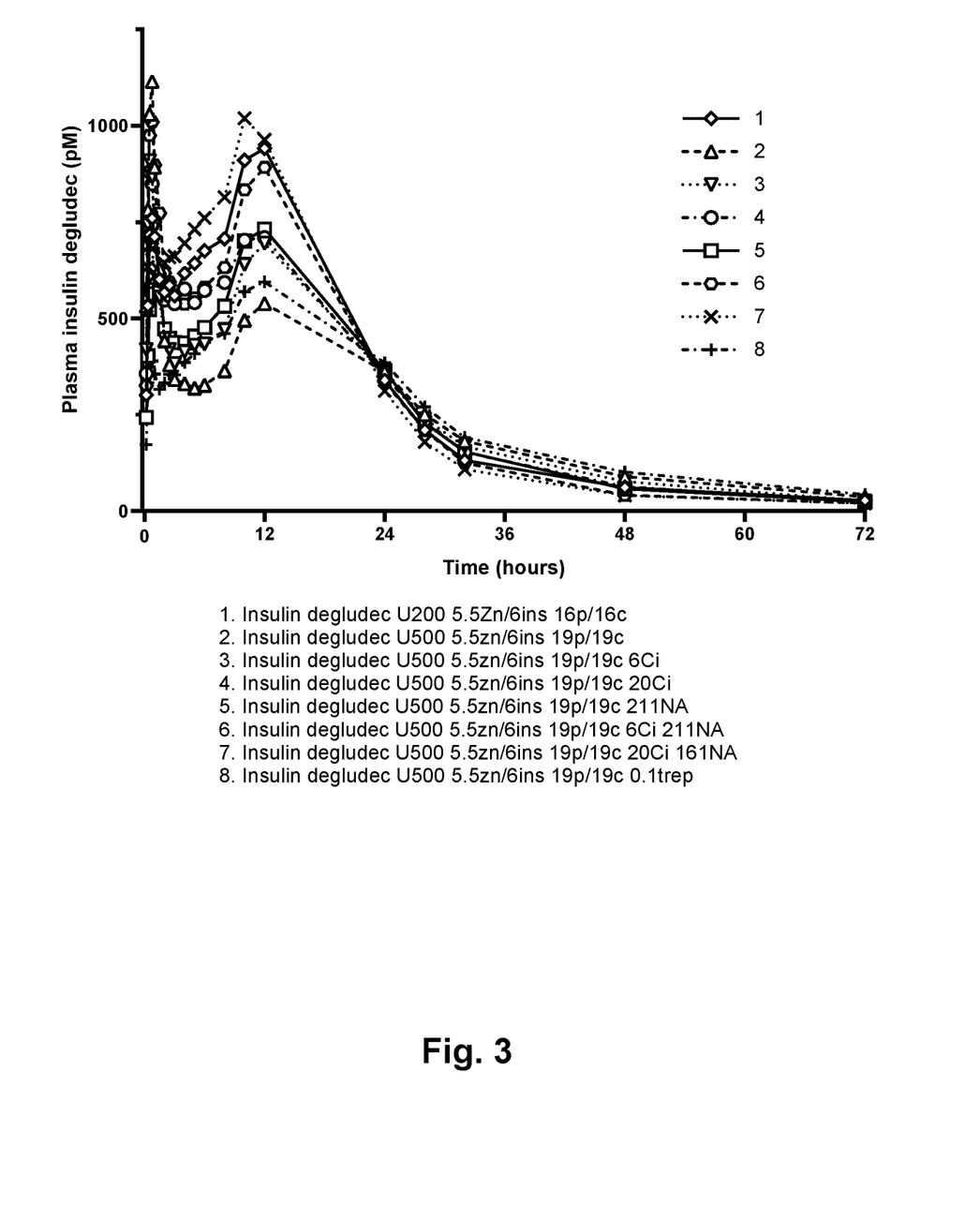
FIG. 3. PK profiles of insulin degludec obtained with the test formulations 1-8 data to 72 hours (mean).

Results:

FIG. 3 shows the PK curves from the experiment JStu190601. Example 2 illustrated how addition of either citrate or niacinamide increased the bioavailability and in JStu190601 we tested combinations of citrate and niacinamide. Table 6 shows how it is possible to titrate the concentrations of citrate and niacinamide to match the AUC of U500 formulations to the U200 formulation. Specifically, neither formulation 6 nor formulation 7, which contained both citrate and niacinamide, were significantly different from formulation 1 with respect to AUC, and numerically, the AUC for the U500 insulin degludec formulation 7 was within 2% of the U200 insulin degludec formulation 1.

Figure 4:
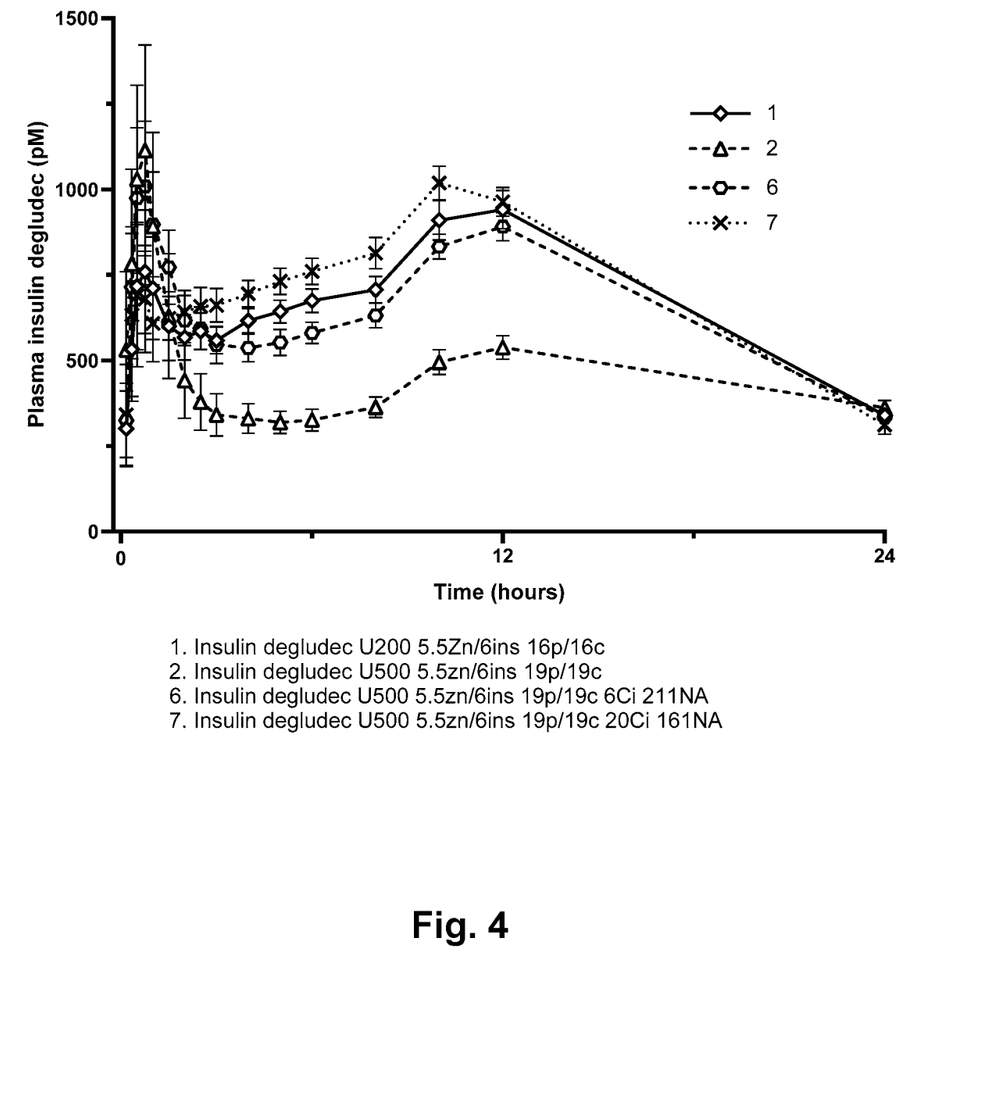
FIG. 4. PK profiles of insulin degludec obtained with the test formulations 1, 2, 6 and 7 data to 24 hours (mean±SEM).

Pigs exhibit an early peak in absorption of insulin degludec that is not seen in humans. The estimation and comparison of Cmax is therefore associated with uncertainty. For clarity, FIG. 4 shows the data for formulations 1, 2, 6 and 7 only with data plotted to 24 hours. Considering the second peak (maximal exposure that occurs around 10-12 hours after dosing), we observed that the reduction in the U500 formulation 2 is approximately 42% to that of the U200 formulation 1 ($p<0.001$). Cmax was increased in the U500 formulation 6 containing 6 mM citrate and 211 mM niacinamide (only 4% reduction compared to formulation 1, not statistically significant) and was further increased in formulation 7 containing 20 mM citrate and 161 mM niacinamide (10% increase compared to formulation 1, not statistically significant).

We note that when adding both niacinamide and citrate to the formulation, it is possible to tune both the AUC and the late Cmax to match the values in the degludec U200 formulation close enough that a degludec U500 formulation with niacinamide and citrate concentrations in the formulation space we have explored can be demonstrated to be bioequivalent to Tresiba® U200 in a clinical trial.

TABLE 6

AUCs calculated by non-compartmental analysis

| | Formulation, study JStu190601 | | | | | | | |
|---|---|---|---|---|---|---|---|---|
| | 1 | 2 | 3 | 4 | 5 | 6 | 7 | 8 |
| AUC ((nM × min), mean ± SD) | 1229 ± 125 | **** 990 ± 125 | ** 1054 ± 102 | ** 1075 ± 168 | **** 1036 ± 110 | ns 1125 ± 132 | ns 1202 ± 112 | *** 1032 ± 134 |
| Percent difference to formulation 1 | | −19% | −14% | −13% | −16% | −8% | −2% | −16% |

Post-hoc comparisons to formuation 1 using ANOVA model
**** $p < 0.0001$
*** $p < 0.001$
** $p < 0.01$
ns not significant at 0.05 level Conclusion Example 4 illustrates that by appropriately chosen combinations of citrate and niacinamide in U500 formulations of insulin degludec, it is possible to match both Cmax and AUC to those of a U200 degludec formulation thereby demonstrating that it is possible to make a U500 formulation of insulin degludec that is bioequivalent to Tresiba® U200.

The invention claimed is:

1. A soluble insulin preparation comprising:
   NεB29-hexadecandioyl-γ-Glu-(desB30) human insulin in a concentration from 1800 nmol/ml to 4200 nmol/ml,
   Zinc ions in a concentration from 4.0 Zn/6Ins to 7.0 Zn/6Ins,
   Niacinamide in a concentration from 110 mM to 220 mM or treprostinil in a concentration from 0.02 µg/ml to 1 µg/ml,
   Citrate in a concentration from 6 mM to 40 mM, and
   pH in the range from 7.0 to 8.0.

2. The soluble insulin preparation according to claim 1, wherein the concentration of said NεB29-hexadecandioyl-γ-Glu-(desB30) human insulin is about 3000 nmol/ml.

3. The soluble insulin preparation according to claim 1, wherein the concentration of said zinc ions is from 5.0 Zn/6Ins to 6.0 Zn/6Ins.

4. The soluble insulin preparation according to claim 1, which comprises niacinamide.

5. The soluble insulin preparation according to claim 1, which comprises niacinamide in a concentration from 135 mM to 195 mM, or from 150 mM to 180 mM.

6. The soluble insulin preparation according to claim 1, which comprises treprostinil.

7. The soluble insulin preparation according to claim 6, which comprises treprostinil in a concentration from 0.02 µg/ml to 0.5 µg/ml.

8. The soluble insulin preparation according to claim 1, which comprises citrate in a concentration from 15 mM to 30 mM.

9. The soluble insulin preparation according to claim 1, which has pH 7.6.

10. The soluble insulin preparation according to claim 1 further comprising a phenolic preservative or a mixture of phenolic preservatives.

11. The soluble insulin preparation according to claim 10 wherein said mixture of phenolic preservatives is phenol and m-cresol.

12. The soluble insulin preparation according to claim 11, wherein the concentration of phenol is from 1.3 mg/ml to 2.0 mg/ml and the concentration of m-cresol is from 1.5 mg/ml to 2.3 mg/ml.

13. The soluble insulin preparation according to claim 1, comprising:
    NεB29-hexadecandioyl-γ-Glu-(desB30) human insulin in a concentration of 3000 nmol/ml,
    Zinc ions in a concentration of 5.5 Zn/6Ins,
    Niacinamide in a concentration of 211 mM,
    citrate in a concentration of 6 mM, and pH of 7.6.

14. The soluble insulin preparation according to claim 1, comprising:
    NεB29-hexadecandioyl-γ-Glu-(desB30) human insulin in a concentration of 3000 nmol/ml,
    Zinc ions in a concentration of 5.5 Zn/6Ins,
    Niacinamide in a concentration of 161 mM,
    citrate in a concentration of 20 mM, and pH of 7.6.

15. A method for treatment of hyperglycemia; stress induced hyperglycemia: type 2 diabetes: impaired glucose tolerance; and type 1 diabetes; burns, operation wounds, and other diseases or injuries where an anabolic effect is needed; myocardial infarction, stroke, coronary heart disease, and other cardiovascular disorders; or critically ill diabetic and non-diabetic patients, comprising administering to the patient in need thereof a pharmaceutically acceptable amount of a soluble insulin preparation according to claim 1.

16. The soluble insulin preparation according to claim 6, which comprises treprostinil in a concentration from 0.04 µg/ml to 0.3 µg/ml.

17. The soluble insulin preparation according to claim 6, which comprises treprostinil in a concentration from 0.05 µg/ml to 0.2 µg/ml.

18. The soluble insulin preparation according to claim 6, which comprises treprostinil ia concentration from 0.1 to 1 µg/ml.

19. The soluble insulin preparation according to claim 1, which comprises citrate in a concentration from 6 mM to 20 mM.

20. The soluble insulin preparation according to claim 1, which comprises citrate in a concentration from 20 mM to 40 mM.

* * * * *

UNITED STATES PATENT AND TRADEMARK OFFICE
CERTIFICATE OF CORRECTION

PATENT NO. : 12,343,383 B2
APPLICATION NO. : 17/626025
DATED : July 1, 2025
INVENTOR(S) : Jeppe Sturis et al.

It is certified that error appears in the above-identified patent and that said Letters Patent is hereby corrected as shown below:

In the Claims

At Column 16, Claim number 15, Line number 18 - 19, Please delete "stress induced hyperglycemia:" and insert --stress induced hyperglycemia;--

At Column 16, Claim number 15, Line number 19, Please delete "type 2 diabetes:" and insert --type 2 diabetes;--

At Column 16, Claim number 15, Line number 20, Please delete "tolerance; and" and insert --tolerance;--

At Column 16, Claim number 18, Line number 35, Please delete "ia" and insert --in a--

Signed and Sealed this
Twentieth Day of January, 2026

John A. Squires
*Director of the United States Patent and Trademark Office*